United States Patent [19]

Ohi et al.

[11] Patent Number: 5,707,827
[45] Date of Patent: Jan. 13, 1998

[54] MUTANT AOX2 PROMOTER, VECTOR CARRYING SAME, TRANSFORMANT AND PRODUCTION OF HETEROLOGOUS PROTEIN

[75] Inventors: Hideyuki Ohi; Masami Miura; Ryuji Hiramatsu; Takao Ohmura, all of Hirakata, Japan

[73] Assignee: The Green Cross Corporation, Osaka, Japan

[21] Appl. No.: 281,025

[22] Filed: Jul. 27, 1994

[30] Foreign Application Priority Data

Jul. 27, 1993 [JP] Japan .................................. 5-185003

[51] Int. Cl.⁶ .......................... C12P 21/02; C12N 15/09; C12N 15/67; C07H 21/04
[52] U.S. Cl. ................. 435/69.1; 435/254.2; 435/254.23; 435/320.1; 536/24.1
[58] Field of Search ..................... 435/69.1, 254.2, 435/254.23, 320.1; 536/24.1

[56] References Cited

FOREIGN PATENT DOCUMENTS

| 0506040 | 9/1992 | European Pat. Off. ......... C12N 15/81 |
| 0595334 | 5/1994 | European Pat. Off. ......... C12N 15/81 |

Primary Examiner—David Guzo
Assistant Examiner—Nancy T. Degen
Attorney, Agent, or Firm—Sughrue, Mion, Zinn, Macpeak & Seas, PLLC

[57] ABSTRACT

A mutant AOX2 promoter wherein 1 to 3 oligonucleotide(s) GATAGGCTATTTTTGTCGCATAAAT (SEQUENCE ID NO: 2) is (are) added in the normal direction, the reverse direction or in both the normal and reverse directions at the 5' end side of a partial DNA fragment of a wild-type AOX2 promoter, a vector carrying the promoter, a transformant into which the vector has been introduced and a method for producing a heterologous protein, comprising culture of the transformant. The mutant AOX2 promoter of the present invention has a markedly enforced promoter activity as compared with wild-type AOX2 promoters. Accordingly, the promoter of the present invention is highly utilizable as a promoter to be carried by a vector capable of expressing a heterologous protein. The vector of the present invention can efficiently express and produce various useful heterologous proteins in hosts.

18 Claims, 20 Drawing Sheets

FIG. 2
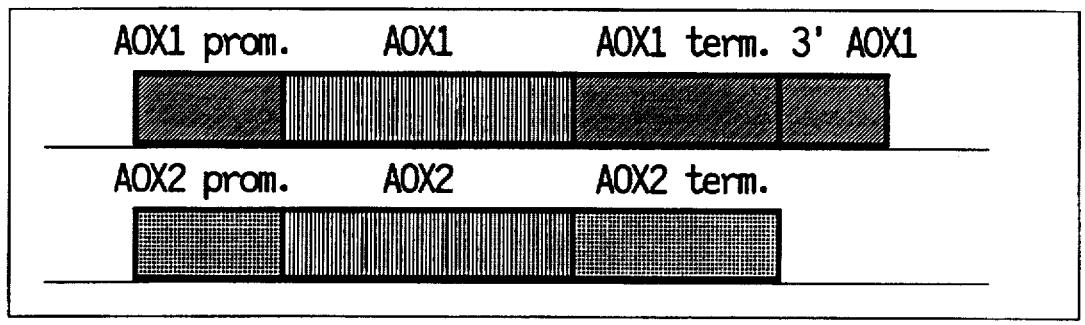
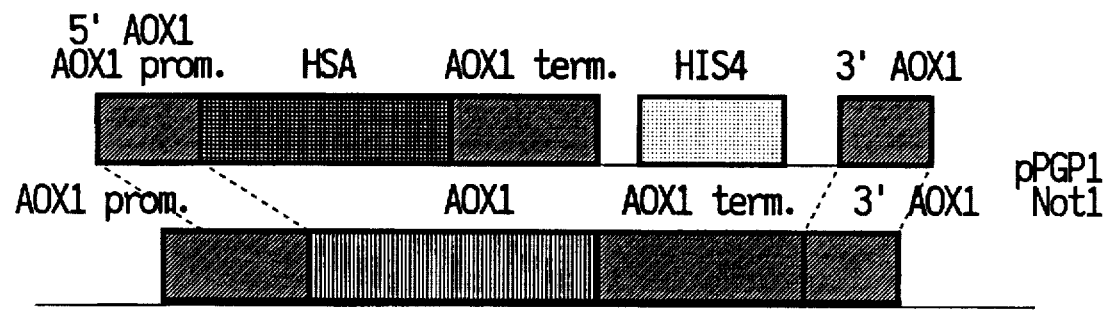
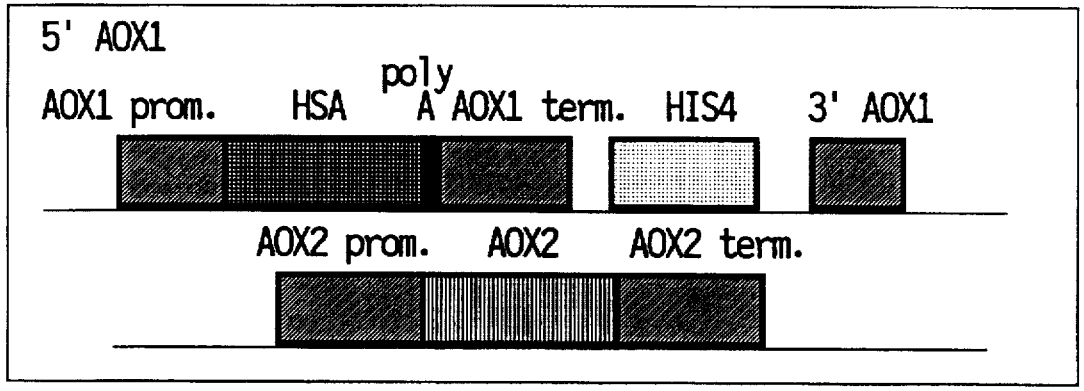

FIG. 9

```
               1189                      1209
5' TTGATAAGAC ATCACCTTCC AAGATAGGCT ATTTTGTGTCG CATAAATTTT TGTC 3'
         5'********** ***G*G**** *******3'                        (25 mer)
                 5' ****** T G*******3'                   (22 mer)

UAS3p
UAS4p
```

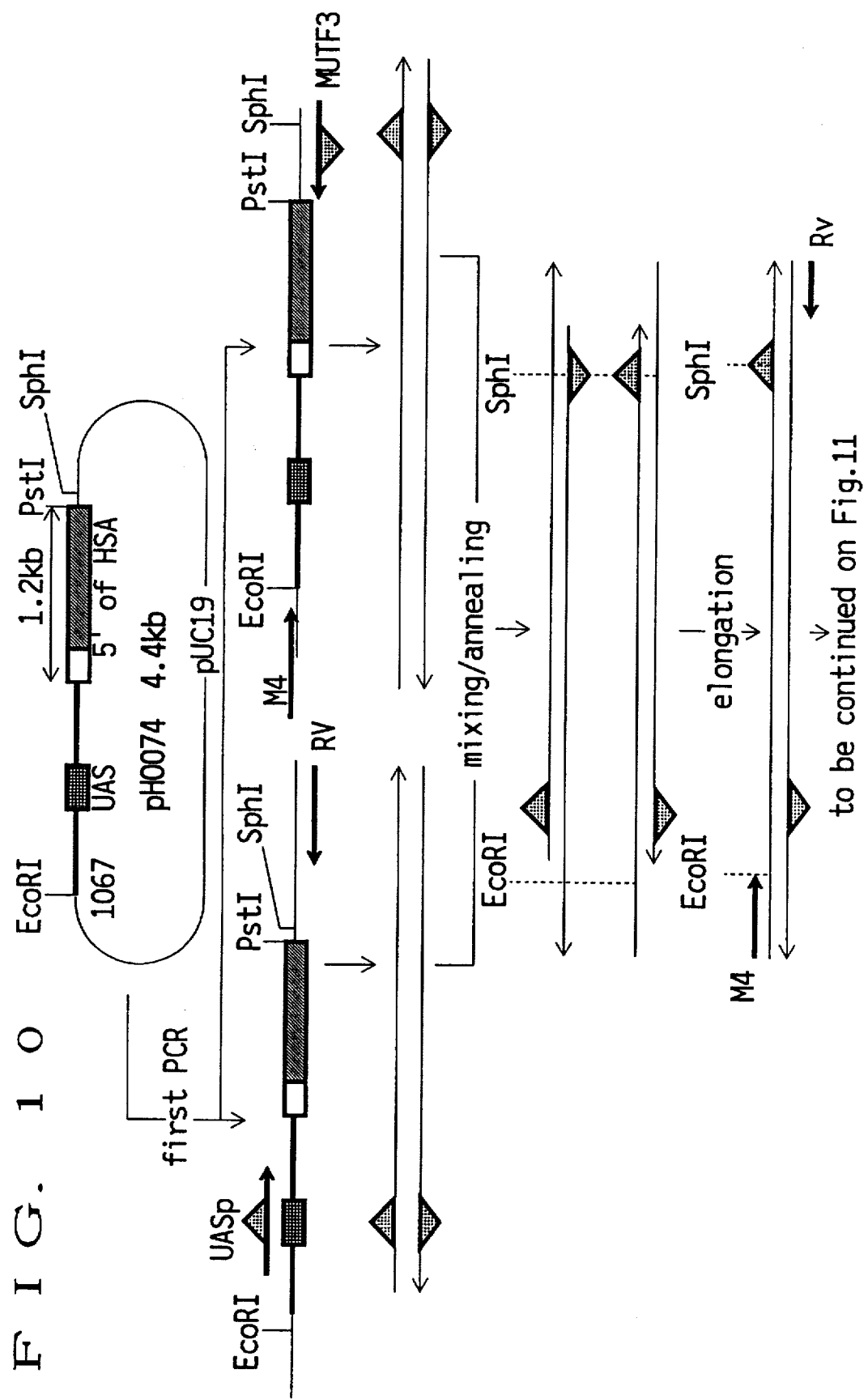

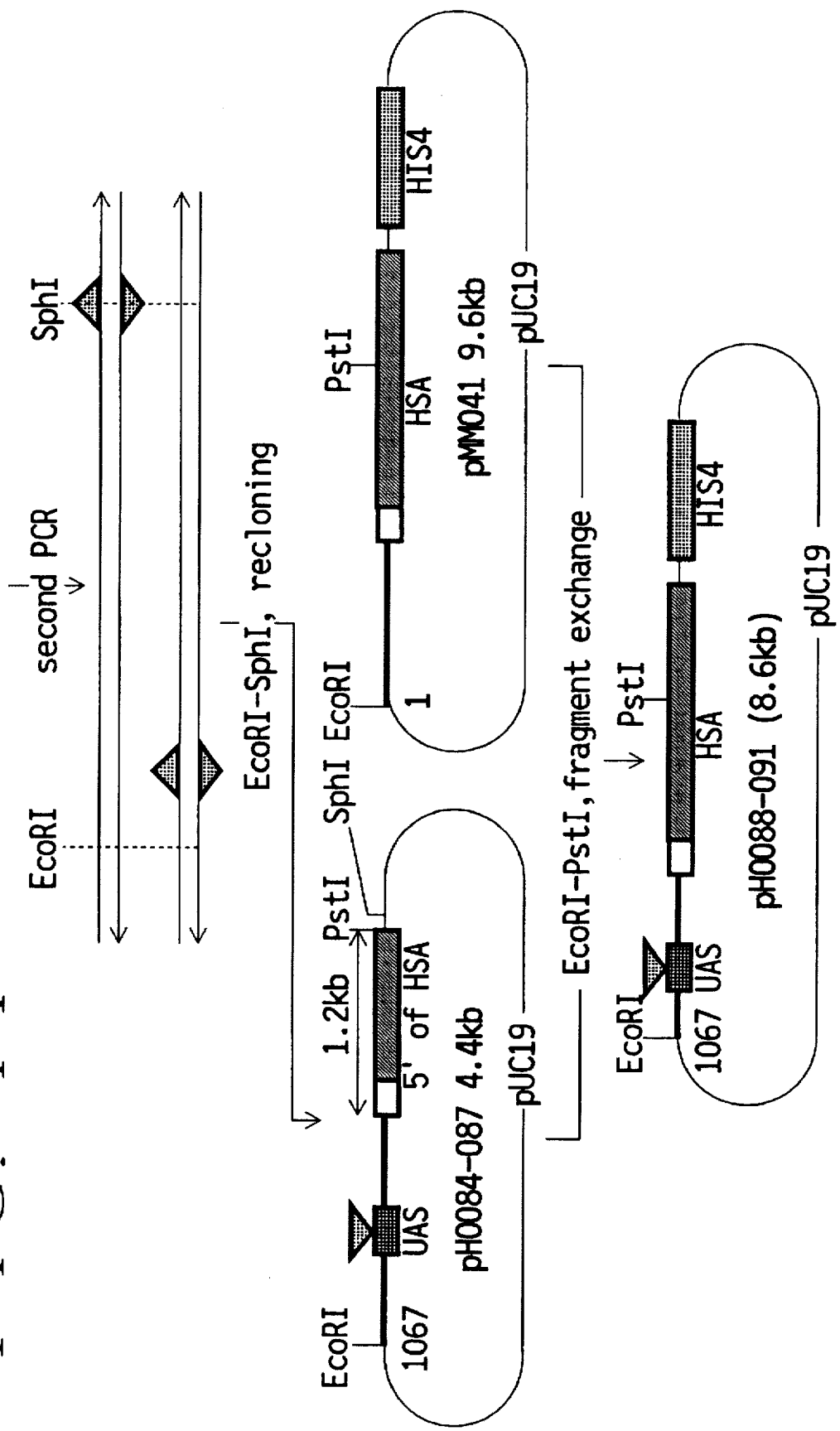
F I G. 1 1

FIG. 16

```
                            1192                                    1216
P. pastoris AOX2   -341 CCAAGATAG- GCTATTTTG -TC--GCATA AATT -312
P. pastoris AOX1   -219 TGCTGATAGC -CTAACGTTC AT---G-ATC AAAA -195
P. pastoris AOX1   -334 AAGCGATAGA GAGACTGCC -TA-AGCATT AATG -365
                                                    (Complementary chain)
```

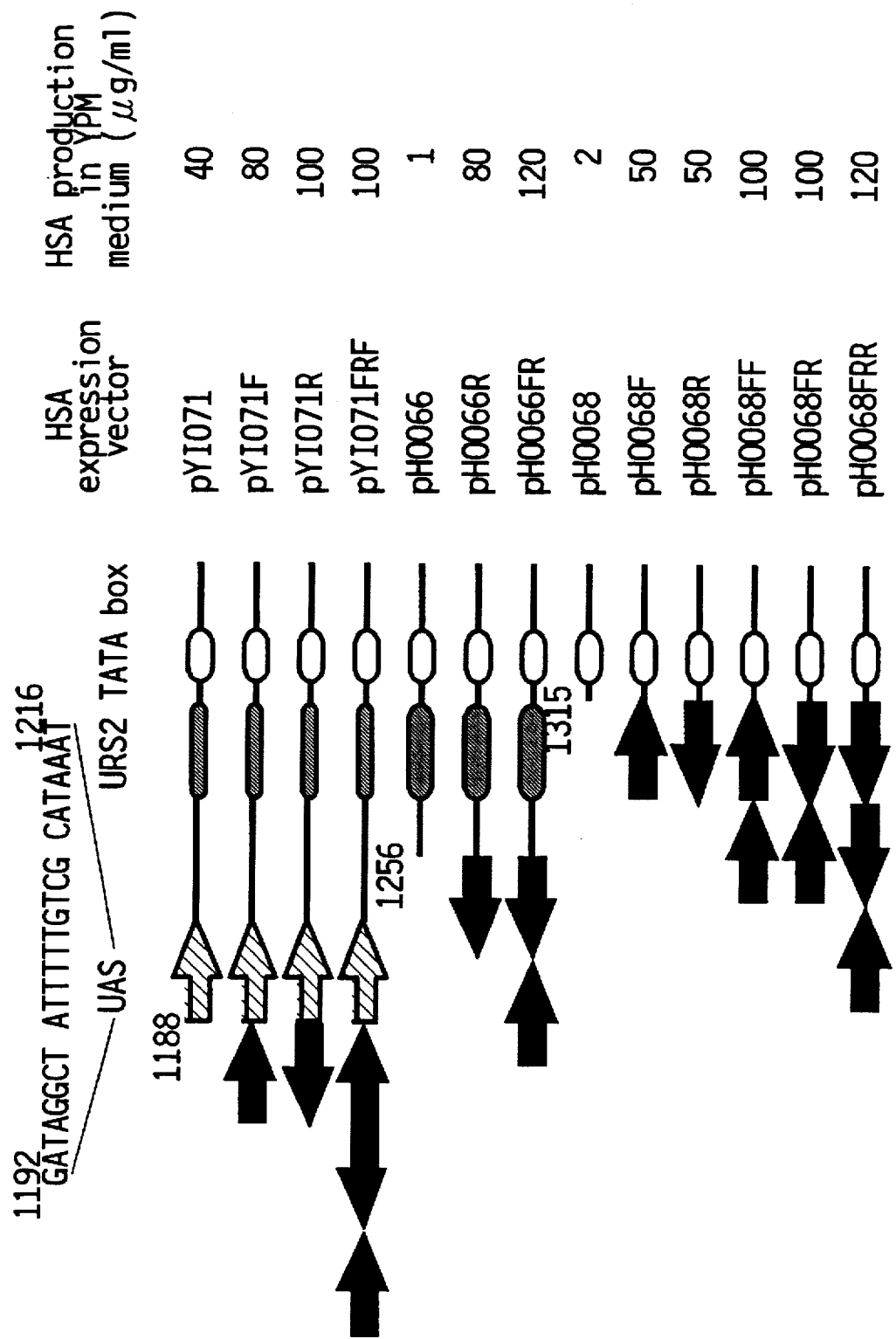

5,707,827

1

MUTANT AOX2 PROMOTER, VECTOR CARRYING SAME, TRANSFORMANT AND PRODUCTION OF HETEROLOGOUS PROTEIN

FIELD OF THE INVENTION

The present invention relates to a mutant AOX2 promoter suitably used for expressing a heterologous gene, a vector carrying said promoter, a transformant into which said vector has been introduced and a method for producing a heterologous protein, comprising culturing said transformant.

BACKGROUND OF THE INVENTION

In the fields of genetic engineering, improvements and development of gene expression systems have been conventionally done in an attempt to increase the expression of gene and the yield of objective proteins. The expression system using, as a host, a methylotrophic yeast is drawing attention as a system for expressing heterologous protein genes.

The methylotrophic yeast is capable of proliferation using methanol as a carbon and energy source. This is attributable to the fact that it has a gene encoding alcohol oxydase (EC1.1.3.B, hereinafter also referred to as AOX) which is an enzyme catalyzing a first reaction in the metabolism of methanol, namely, oxidation of methanol into formaldehyde.

*Pichia pastoris* is one of the methylotrophic yeasts and has two kinds of AOX genes, AOX1 gene and AOX2 gene, each known as having a peculiar promoter at 5' end side nontranslation region (AOX1 promoter, AOX2 promoter). An AOX2 promoter has an extremely weak transcription activity, making sharp contrast with an AOX1 promoter having a strong transcription activity, and AOX actually expressed and produced is mostly derived from the AOX1 gene [Molecular and Cellular Biology, Vol. 9, 1316 (1989)].

For the production of a heterologous protein by the use of a Pichia yeast, conventionally, an AOX1 promoter having a strong transcription activity is used. In recent years, moreover, methods for producing heterologous proteins by using the regulatory region of said AOX genes have been studied [Yeast, 5, 167–177 (1989), EP-A-344459, EP-A-347928]. There is a strong demand for a promoter having a strong transcription activity to magnify the expression of the heterologous protein.

SUMMARY OF THE INVENTION

An object of the present invention is to provide a promoter useful for a large-scale production of a heterologous protein, a vector carrying said promoter, and a transformant into which said vector has been introduced. Also, the present invention aims at establishing a method for producing a heterologous protein, comprising culturing said transformant.

As a result of the intensive study of the present inventors, it has been found that the use, as a promoter, of a DNA fragment obtained by inserting (a) nucleotide sequence(s) comprising a specific nucleotide sequence at an upstream from a partial DNA fragment of a wild-type AOX2 promoter results in efficient expression of a heterologous protein located downstream therefrom and the present invention has been completed based on such finding.

According to the present invention, there is provided a mutant AOX2 promoter having a nucleotide sequence obtained by adding 1 to 3 oligonucleotide sequences, the

2 sequence being GATAGGCTATTTTTGTCGCATAAAT [SEQ. ID NO: 2 hereinafter referred to as oligonucleotide (D)], to a partial DNA fragment of a wild-type AOX2 promoter having the nucleotide sequence of SEQ. ID NO:1, in the forward and/or reverse direction(s) at the 5' end thereof.

The present invention also provides a vector carrying said mutant AOX2 promoter, a transformant into which said vector has been introduced, and a method for producing a heterologous protein, comprising culturing said transformant.

BRIEF DESCRIPTION OF THE DRAWINGS

FIG. 2 shows an AOX1 gene region and an AOX2 gene region of PC4130 strain wherein term. means terminator and prom. means promoter.

FIG. 9 shows nucleotide sequences of two primers for the introduction of site-directed mutation, (SEQ ID NOS:16 and 17, wherein the uppermost sequence is AOX2 promoter, SEQ ID NO:1. Following the names of two primer UASps, the nucleotide sequences thereof are given. In the Figure, * designates the same nucleotide as that of the AOX2 promoter.

FIG. 10 shows the construction of an HSA expression vector (e.g. pHO090) carrying AOX2 promoter having a mutant UAS region.

FIG. 11 shows the construction of an HSA expression vector (e.g. pHO090) carrying AOX2 promoter having a mutant UAS region.

FIG. 16 shows the homology of nucleotide sequences of a part of the AOX2 promoter (nucleotides 1188–1217 of SEQ ID NO:1) and parts of the AOX1 promoter (SEQ ID NO:22 and SEQ ID NO:23).

FIG. 19 shows the structure of a mutant AOX2 promoter having a synthetic DNA fragment putatively having UAS sequence, SEQ ID NO:2, at the 5' end and HSA produced thereby.

DETAILED DESCRIPTION OF THE INVENTION

Figure 1:
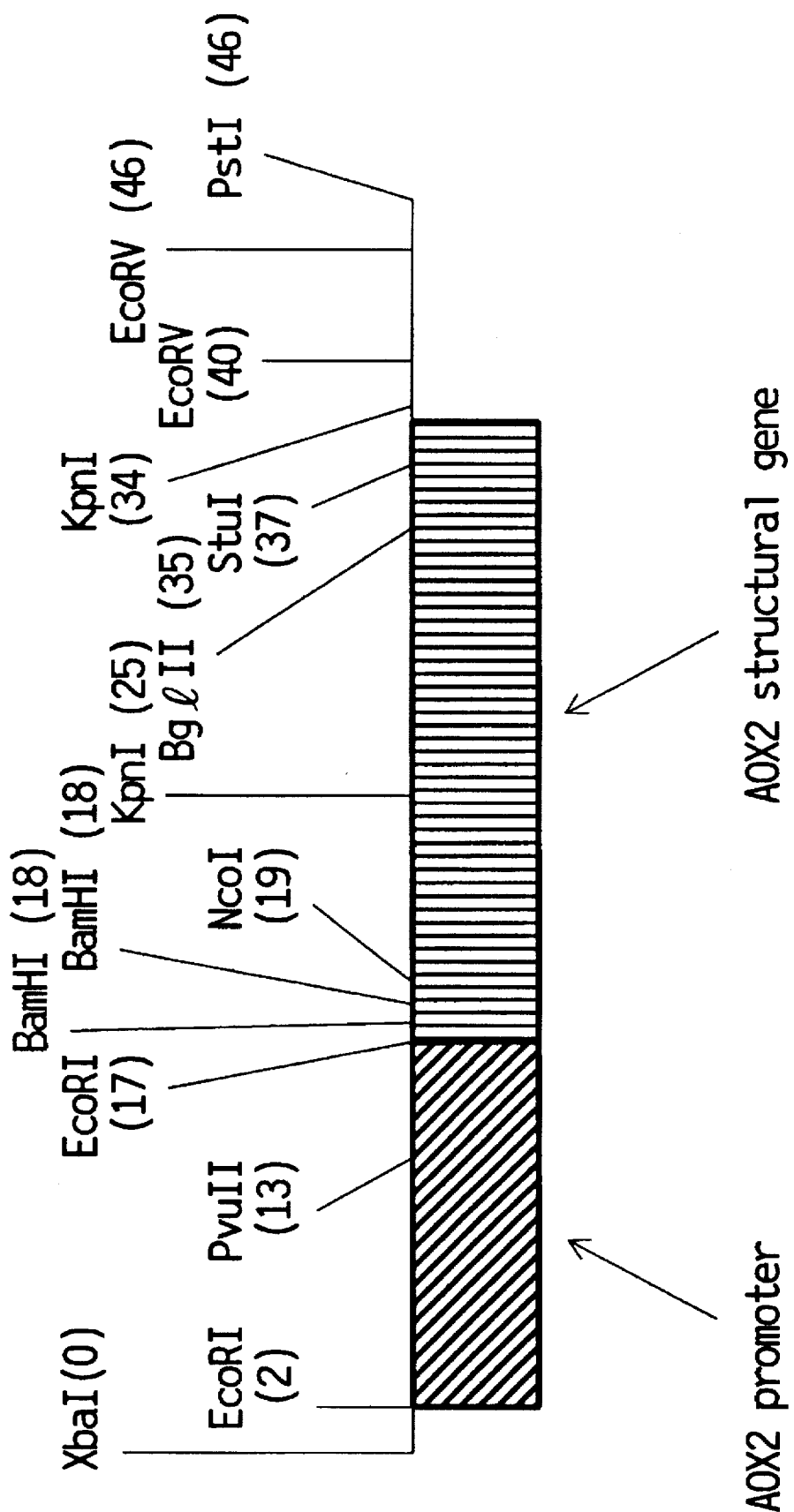
FIG. 1 shows a restriction enzyme map of the region of AOX2 gene and its vicinity, wherein the figures in parentheses indicate the distance (×100 nucleotide) when XbaI recognition site is taken as 0.

When the present invention has been completed, the inventors first analyzed the function of a wild-type AOX2 promoter. As a result, a portion enhancing the promoter transcription activity (hereinafter referred to as UAS region), two portions suppressing the activity (hereinafter referred to as URS1 region and URS2 region) and the location of TATA region have been found. In the present invention, URS1 region refers to nucleotides 845–960 of a wild-type AOX2 promoter (Sequence Listing, Sequence No. 1), UAS region refers to nucleotides 1192–1216 thereof, URS2 region refers to nucleotides 1274–1314 thereof and TATA region refers to nucleotides 1325–1330.

Unless specificaly noted, nucleotide number refers to that used for wild-type AOX2 promoter nucleotides (Sequence Listing, Sequence No. 1).

In the present invention, the partial DNA fragment of wild-type AOX2 promoter refers to a DNA fragment lacking a certain region of the wild-type AOX2 promoter and includes the following.

(1) A DNA fragment lacking the region upstream from the URS1 region (nucleotides 845–960) of the wild-type AOX2 promoter (hereinafter referred to as partial DNA fragment 1, which includes URS1 region, UAS region, URS2 region and TATA region). That is, the fragment lacks all or part of the region upstream from nucleotide 845. The region laking therefrom is not limited insofar as it is located upstream from the URS1 region. Such a DNA fragment only needs to have at least a nucleotide sequence 845–1528.

(2) A DNA fragment lacking the region upstream from the UAS region (nucleotides 1192–1216) including the URS1 region of the wild-type AOX2 promoter (hereinafter referred to as partial DNA fragment 2, which includes UAS region, URS2 region and TATA region). That is, the fragment lacks all or part of the region upstream from nucleotide 1192. The region laking therefrom is not limited insofar as it is located upstream from the UAS region and includes the URS1 region. Such a DNA fragment only needs to have at least a nucleotide sequence 1192–1528.

(3) A DNA fragment lacking the region located upstream from the URS2 region (nucleotides 1274–1314) including the URS1 region and the UAS region of the wild-type AOX2 promoter (hereinafter referred to as partial DNA fragment 3, which includes URS2 region and TATA region). That is, the fragment lacks all or part of the region upstream from nucleotide 1274. The region laking therefrom is not limited insofar as it is located upstream from the URS2 region and includes the URS1 region and the UAS region. Such a DNA fragment only needs to have at least a nucleotide sequence 1274–1528.

(4) A DNA fragment lacking the region located upstream from the TATA region (nucleotides 1325–1330) including the URS1 region, the UAS region and the URS2 region of the wild-type AOX2 promoter (hereinafter referred to as partial DNA fragment 4, which includes TATA region). That is, the fragment lacks all or part of the region upstream from nucleotide 1325. The region laking therefrom is not limited insofar as it is located upstream from the TATA region and includes URS1 region, UAS region and URS2 region. Such a DNA fragment only needs to have at least a nucleotide sequence 1325–1528.

The partial DNA fragment as referred to in the present invention may be a nucleotide sequence derived from the wild-type AOX2 promoter, which is partially substituted, deleted or added. The sites of substitution, deletion and addition, as well as occurrence thereof are not limited and such mutations may occur in URS1 region, UAS region, URS2 region or other region.

As exemplary mutations, the followings are given. A. Substitution of part(s) of the nucleotide sequence in the URS2 region The substitution site is not subject to any limitation so long as it is in the URS2 region. In this region, one or more nucleotides may be substituted and the substitution site may be one or more. Specifically, a DNA fragment having the 1274th thymine (T) substituted with cytosine (C) is exemplified. B. Addition of new oligonucleotide(s) in the URS2 region The addition site is not subject to any limitation so long as it is in the URS2 region. In this region, any number of nucleotides may be added and the addition site may be one or more. Specifically, a DNA fragment having a 19 bp oligonucleotide (SEQ ID NO:3) corresponding to the 1296–1314 nucleotides inserted between the 1314th and the 1315th nucleotides in duplicate is exemplified. C. Substitution of part(s) of the nucleotide sequence in the UAS region The substitution site is not subject to any limitation so long as it is in the UAS region. In this region, one or more nucleotides may be substituted and the substitution site may be one or more. Specifically, a DNA fragment wherein the 1209th guanine (G) has been substituted with thymine (T), 1212nd thymine (T) has been substituted with guanine (G) and 1193rd and 1195th adenines (A) have been respectively substituted with guanine (G) is exemplified.

The mutant AOX2 promoter of the present invention has a sequence wherein the oligonucleotide(s) (I) has(have) been added to a partial DNA fragment of a wild-type AOX2 promoter at the 5' end thereof in the forward and/or reverse direction(s).

Addition of the oligonucleotide (I) in the forward direction means that the oligonucleotide (I) is coordinated, at the 5' end thereof, with an AOX2 promoter lacking the upstream region to make 5'-GATAGGCTATTTTTGTCGCATAAAT-3' (SEQ ID NO:2). Addition of the oligonucleotide (I) in the reverse direction means that the oligonucleotide (I) is coordinated, at the 5' end thereof, with an AOX2 promoter lacking the upstream region to make 3'-GATAGGCTATTTTTGTCGCATAAAT-5' (SEQ ID NO:2).

Specific examples of the mutant AOX2 promoter of the present invention include the following.

I. A promoter wherein the oligonucleotide (I) is added in the forward or reverse direction at the 5' end of the partial DNA fragment 1.

An example thereof is a promoter wherein the oligonucleotide (I) is added in the forward or reverse direction at the 5' end of the partial AOX2 promoter fragment of 726–1528 nucleotides.

II. A promoter wherein the oligonucleotide (I) is added in the forward or reverse direction at the 5' end of the partial DNA fragment 2.

Examples thereof are a promoter wherein the oligonucleotide (I) is added in the forward or reverse direction at the 5' end of the partial AOX2 promoter fragment of 1063–1528 nucleotides and a promoter wherein the oligonucleotide (I) is added in the forward or reverse direction at the 5' end of the partial AOX2 promoter fragment of 1188–1528 nucleotides.

III. A promoter wherein the oligonucleotide (I) is added in the forward or reverse direction at the 5' end of the partial DNA fragment 3.

An example thereof is a promoter wherein the oligonucleotide (I) is added in the forward or reverse direction at the 5' end of the partial AOX2 promoter fragment of 1256–1528 nucleotides.

IV. A promoter wherein the oligonucleotide (I) is added in the forward or reverse direction at the 5' end of the partial DNA fragment 4.

An example thereof is a promoter wherein the oligonucleotide (I) is added in the forward or reverse direction at the 5' end of the partial AOX2 promoter fragment of 1315–1528 nucleotides.

The mutant AOX2 promoter of the present invention may have plural, preferably 2–3 oligonucleotides (I) in linkage at the 5' end of the partial DNA fragment of an AOX2 promoter lacking the upstream region in a manner as described earlier. When plural oligonucleotides (I) are ligated, the direction of the nucleotide sequences is not subject to any limitation and it may be in the forward or reverse direction, or in the both directions.

In the present invention, (1) the mutant AOX2 promoter, (2) a vector carrying said promoter and (3) a transformant into which said vector has been introduced are prepared, for example, as follows.

(I) Mutant AOX2 promoter

The mutant AOX2 promoter of the present invention can be prepared by adding a chemically-synthesized oligonucleotide (I) to a partial DNA fragment at the 5' end, which is obtained by processing a wild-type AOX2 promoter by genetic engineering. The partial DNA fragment can be prepared by subjecting a certain portion of the nucleotide sequence of the wild-type AOX2 promoter to deletion, substitution or addition of new nucleotides. The treatment is done by conventional genetic engineering, and site-directed deletion [Nucl. Acids Res., 11, 1645 (1983)], site-directed mutagenesis, restriction enzyme treatment, treatment with synthetic gene or PCR method may be used for this end.

The promoter may be also prepared by chemical synthesis based on the nucleotide sequence of the mutant AOX2 promoter of the present invention.

Alternatively, so as to express and produce alcohol oxidase from an AOX2 gene alone since an AOX1 gene has been genetically deteriorated, a strain with poor methanol utilization may be subcultured in a medium containing methanol as a sole carbon source to cause mutation into a strain with improved methanol utilization (Super High Grade Strain; SHG strain), from which a partial DNA fragment (partially mutated AOX2 promoter) is obtained and a chemically-synthesized oligonucleotide (I) is added at the 5' end thereof to give the mutant AOX2 promoter of the invention.

(II)

(i) Construction of recombinant vector

The thus-obtained mutant AOX2 promoter is inserted into a suitable plasmid vector or a phage vector and used as a vector for expressing a heterologous protein.

The insertion of said promoter into various plasmids and phages can be done according to a conventional method for DNA recombination such as a method described in Molecular Cloning (Cold Spring Harbor Lab., 1989).

(ii) Construction of recombinant expression vector

The recombinant expression vector of the present invention, with which a heterologous protein gene is expressed under the control of the mutant AOX2 promoter, can be constructed by inserting a gene of the desired heterologous protein into a 3'-flanking region of the mutant AOX2 promoter in the recombinant vector obtained as above, via a translation initiation codon.

Alternatively, it may be constructed by cleaving out the mutant AOX2 promoter of the present invention from the above-mentioned recombinant plasmid vector or phage vector by using a restriction enzyme, and replacing a promoter region of a vector having a structural gene for a heterologous protein with the mutant AOX2 promoter by using a restriction enzyme, DNA ligase, etc.

More specifically, the vector of the present invention is constructed in such a manner that (1) mutant AOX2 promoter, (2) ribosome binding site, (3) translation initiation codon, (4) DNA having nucleotide sequence encoding signal peptide, (5) DNA having nucleotide sequence encoding heterologous protein, (6) translation termination codon, (7) terminator, (8) selection marker gene, (9) autonomously replicating sequence, and (10) homologous region are sequentially comprised as necessary in the direction to the downstream, for the efficient expression of a heterologous protein.

There is imposed no particular limitation on the structural gene so long as it encodes the desired heterologous protein such as human serum albumin, prourokinase, tissue plasminogen activator, hepatitis B surface antigen, and various interferons, and it may be prepared by any method. Particularly, cDNA synthesized from mRNA, genomic DNA, chemically-synthesized DNA and DNA constructed by combining these are examplified.

Specific examples include HSA structural gene, AOX1 structural gene and AOX2 structural gene.

The above-mentioned structural gene may have ATG as a translation initiation codon at the 5' terminal of the gene, and it may have a translation termination codon at the 3' terminal of the gene. Examples of the translation termination codon include TAA, TGA, and TAG. One or more of these codons may be combinedly incorporated in each region, and are subject to no limitation.

There is no particular limitation imposed on the terminator insofar as it suits a host to be used for the expression of a nucleotide sequence encoding the desired heterologous protein. For example, AOX1 terminator or AOX2 terminator may be used.

Examples of the selection marker gene are antibiotic-resistant gene and auxotrophic gene. In general terms, when the host is a bacterium, an antibiotic-resistant gene may be used, and examples thereof include cycloheximide-resistant gene, ampicillin-resistant gene, chloramphenicol-resistant gene, bleomycin-resistant gene, hygromycin-resistant gene, and G-418 resistant gene. When the host is other than bacteria, such as a yeast, an auxotrophic gene may be used, and examples thereof include HIS4, URA3, LEU2, and ARG4. These selection markers are preferably incorporated solely or in combination into suitable sites in said vector.

Specific examples of the homologous locus to be integrated into the host chromosome are HIS4, URA3, LEU2, ARG4, and TRP1.

The vector of the present invention may comprise several mutant AOX2 promoters of the invention which are linked (i.e. tandem dimer, tandem trimer). In this case, it is preferable that translation initiation codon be not interposed between the promoters.

(III) transformant and its culture

The transformant of the present invention is prepared by introducing the recombinant expression vector as obtained above into a suitable host cell.

More detailedly, the transformant of the present invention is prepared by introducing the recombinant expression vector of (II) above into a host by a known method such as competent cell method (J. Mol. Biol., 53, 154, 1970), protoplast polyethylene fusion method (Proc. Natl. Acad. Sci. U.S.A., 75, 1929, 1978), lithium acetate method [J. Bacterial., 153, 163 (1983)], calcium phosphate method (Science, 221, 551, 1983), DEAE dextran method (Science, 215, 166, 1982), Electric pulse method (Proc. Natl. Acad. Sci. U.S.A., 81, 7161, 1984), in vitro packaging method (Proc. Natl. Acad. Sci. U.S.A., 72, 581, 1975), virus vector method (Cell, 37, 1053, 1984), or microinjection method (Exp. Cell. Res., 153, 347, 1984).

As the host to be used, a microorganism such as *Echerichia coli, Bacillus subtilis,* or yeast is exemplified, with preference given to a yeast, specifically Pichia yeast, GTS115 (NRRL deposit number Y-15851).

The vector introduced in a host cell may be integrated into a chromosome by insertion or replacement. Or, it may be present as a plasmid.

The number of copies of an exogenous gene to be introduced into a host may be single or plural.

The transformant thus obtained is cultivated in a suitable, known medium selected according to the host to be used for the production of the desired recombinant heterologous protein. The medium contains carbon source, nitrogen source, minerals, vitamins, and drugs essential for the growth of said transformant.

Examples of the medium include LB medium (manufactured by Nissui Seiyaku, Japan) and M9 medium (J. Exp. Mol. Genet., Cold Spring Harbor Laboratory, New York, p. 431, 1972) when the host is *Escherichia coli;* and YPD medium (1% bacto yeast extract, 2% bacto peptone, 2% glucose), YPG medium (1% bacto yeast extract, 2% bacto peptone, 2% glycerol), YPM medium (1% bacto yeast extract, 2% bacto peptone, 2% methanol), YPDM medium (1% bacto yeast extract, 2% bacto peptone, 2% dextrose, 2% methanol), YNB liquid medium containing 0.1–5% methanol (0.7% yeast nitrogen base, manufactured by Difco), YP medium containing 0.01–5% methanol (1% bacto yeast extract, manufactured by Difco, 2% Poly Peptone (manufactured by Daigo Eiyosha, Japan), and SMM medium (2% methanol, 0.5% $CH_3COONH_4$ synthetic medium) when the host is a yeast.

Cultivation is usually carried out at a temperature between 15° C. and 45° C., preferably about 30° C. for 20–360 hours, and aeration and/or agitation may be applied where necessary. The pH of the culture is preferably from 5 to 8.

After culture, the desired heterologous protein accumulated in the culture supernatant or transformant is extracted and purified by known methods. For example, salting-out, solvent precipitation, dialysis, ultrafiltration, gel electrophoresis, gel filtration chromatography, ion exchange chromatography, reverse phase chromatography, affinity chromatography, and so on may be used in combination.

Note that various techniques, reactions, and analysis methods to be used in the present invention are known to those of ordinary skill in the art. Also, enzymes, plasmids, hosts, and the like are commercially available.

The present invention is hereinbelow more detailedly described by way of examples and experimental examples, to which the invention is not limited.

All the enzymes used in the following examples and experimental examples were obtained from commercial supply sources such as Takara Shuzo Kabushiki Kaisha, Japan, unless speicifically identified.

Buffers for enzyme reactions and reaction conditions followed manufacturer's recommendations for each enzyme unless particularly specified.

*Pichia pastoris* GTS115, PC4130, PC4105, and plasmid pPGP1 were obtained from Phillips Petroleum.

Transformation of *Echerichia coli* using a plasmid as a vector, plaque hybridization, and electrophoresis were conducted according to the method described in Molecular Cloning, Cold Spring Harbor Laboratory (1982).

EXAMPLE 1

Cloning of AOX2 gene, and preparation of recombinant vector

The sequence of and a restriction enzyme map of AOX2 gene and its vicinity have been reported by Cregg et al., Mol. Cell. Biol., 9, 1316–1323 (1989) and Koutz et al., YEAST, 5, 167–177 (1989). Referring to the reports, cloning of AOX2 gene was designed. The restriction enzyme map of AOX2 gene and its vicinity is shown in FIG. 1.

First, a chromosome DNA was extracted from PC4130 strain and purified according to the method of Cameron et al. [Nucleic Acids Res., 4, 1429 (1977)].

The PC4130 strain comprises a gene region which was obtained by replacing a part of the AOX1 gene region of GTS115 (HIS4) with a NotI-fragment of pPGP1 plasmid (a plasmid having a transcription unit to permit HSA expression under the control of AOX1 promoter) (FIG. 2).

This chromosome DNA was completely digested with restriction enzymes XbaI and PstI in such a manner that AOX2 promoter region, AOX2 structural gene, and AOX2 terminator region are completely included therein.

The DNA fragment thus obtained was precipitated with ethanol, centrifuged, dried, and dissolved in sterile water. Then, EcoRI methylase (manufactured by Takara Shuzo Kabushiki Kaisha, Japan) was added thereto and allowed to react. Thereafter, TE saturated phenol. chloroform extraction, and chloroform extraction were sequentially conducted. The water layer was subjected to ethanol precipitation, centrifuged, dried, and dissolved in sterile water. Using a DNA blunting kit (manufactured by Takara Shuzo gabushiki Kaisha, Japan), DNA fragment ends were blunted, and ligated with EcoRI linker d(pG-G-A-A-T-T-C-C) (manufactured by Takara Shuzo Kabushiki Kaisha, Japan) using a DNA ligation kit (manufactured by Takara Shuzo Kabushiki Kaisha, Japan). Ethanol precipitation was again conducted. After centrifugation and drying, the precipitate was dissolved in sterile water, to which was added EcoRI, and incubation was done at 37° C. for 1 hour. The mixture was subjected to 1% agarose gel electrophoresis; the band corresponding to 4–5 kb was cut out from the agarose gel; and DNA was recovered from the gel by elution and purification using GENE CLEAN II (manufactured by BIO 101). The obtained DNA was dissolved in sterile water.

The purified DNA fragment was ligated with λgt10 arms (Protoclone™ System, manufactured by Promega), and subjected to in vitro packaging using Gigapack-GOLD3 (manufactured by Stratagene).

The recombinant phage was infected to *E. coli* C600hfl strain which had been adjusted to $A_{600}$=2, and inoculated on an NZY plate (1% NZ amine, 0.5% sodium chloride, 0.5% yeast extract, 0.02% magnesium sulfate, 1.5% agar powder) such that about 500 plaques were grown on each plate. From the plaques grown, clones containing the above-mentioned DNA fragment (positive clone) were selected and obtained by colony hybridization method. That is, using four nylon membranes Colony/Plaque Screen™ (manufactured by NEN), the plaques were transferred to the membranes, followed by denaturation, neutralization, and immobilization. As a prove, used was a fragment obtained by digesting, with EcoRV and BalII, the former half of an AOX1 structural gene derived from *Pichia pastoris*, and then labelling the gene with $^{32}P$ using a random primer labelling kit (manufactured by Takara Shuzo Kabushiki Kaisha). Prehybridization was conducted in a solution of 1% BSA, 1 mM EDTA, 0.5M $NaH_2PO_4$ (pH 7.2), and 7% SDS at 65° C. for 5 minutes. Hybridization was conducted in a solution of 1% BSA, 1 mM EDTA, 0.5M $NaH_2PO_4$ (pH 7.2), 7% SDS, and $^{32}P$-probe at 65° C. overnight, which was followed by incubation/washing in a solution of 0.5M $NaH_2PO_4$ (pH 7.2) at room temperature for 10 minutes, and further incubation (3 times) in a solution of 0.5% BSA, 1 mM EDTA, 40 mM $NaH_2PO_4$ (pH 7.2), and 5% SDS at 37° C. for 30 minutes. The filter was air-dried, and left layered on an X-ray film in an X-ray film exposure cassette at −80° C. for 16 hours for autoradiography. As a result, 2 positive clones were obtained. One of them was cultivated to allow growth of phages to extract phage DNA. The DNA was cleaved with EcoRI, and subjected to agarose electrophoresis to confirm presence of the desired fragments (1.5 kb and 2.9 kb).

Figure 3:
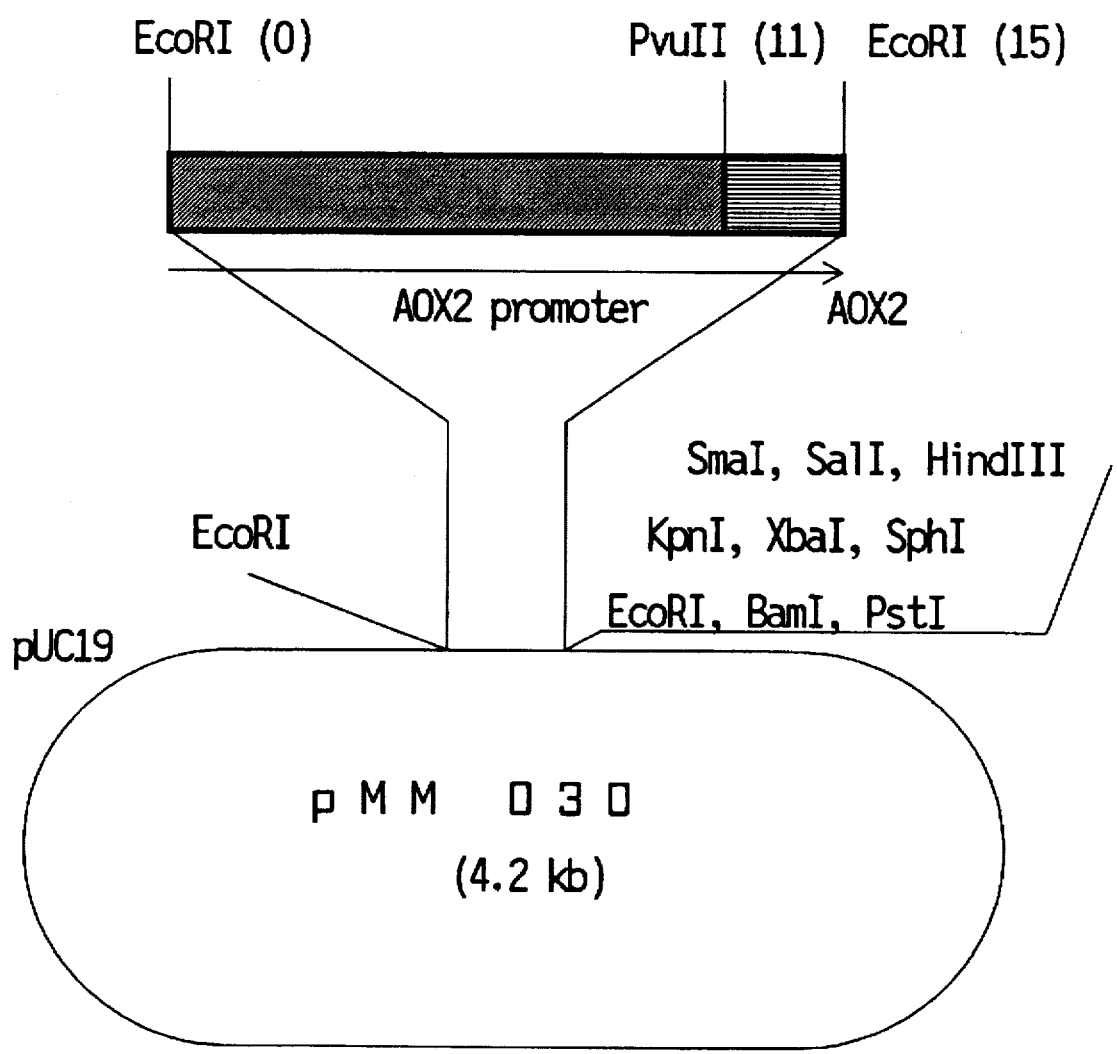
FIG. 3 shows a restriction enzyme map of the AOX2 promoter cloned in pMM030 plasmid, where the figures in parentheses indicate the distance (×100 nucleotide) when EcoRI recognition site is taken as 0.
Figure 4:
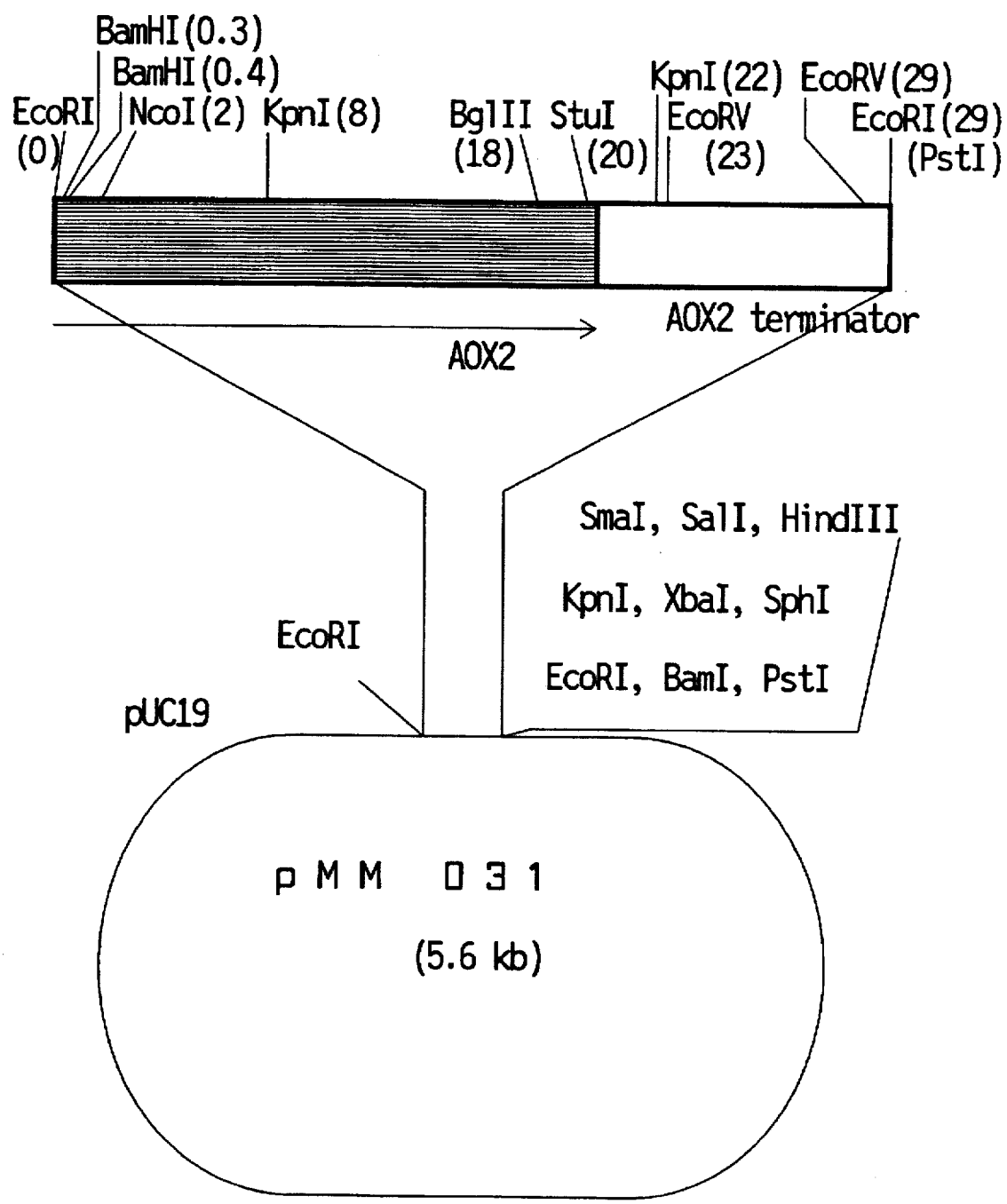
FIG. 4 shows a restriction enzyme map of the AOX2 gene cloned in pMM031 plasmid, where the figures in parentheses indicate the distance (×100 nucleotide) when EcoRI recognition site is taken as 0.

On the other hand, plasmid pUC19 (manufacture by Bethesda Research Laboratories) having an ampicillin-resistant gene as a selection marker was cleaved with EcoRI, treated with alkali phosphatase, and recovered. The DNA fragment obtained from the above-mentioned phage and digested with EcoRI was ligated with the EcoRI-cleaved plasmid to construct a plasmid vector, which was then introduced into *E coli* HB101 to give a transformant. The transformant was inoculated on an L plate containing 40 µg/ml ampicillin and cultured at 37° C. overnight. [The L plate was prepared as follows. Tris base 0.62 g, polypeptone 10 g, yeast extract 5 g, and sodium chloride 5 g were dissolved in water to make the total amount 1 l, and thereto was added 15 g of agar powder, followed by autoclave. After cooling, ampicillin was added, and the mixture was dispensed to a plastic Schale and immobilized to give a plate.] The colonies were screened (EcoRI-digested fragment was confirmed by miniprep) and it was confirmed that clones carrying pUC19 containing 1.5 kb fragment and 2.7 kb fragment were obtained. The clones were subjected to shake culture at 37° C. overnight in a 40 µg/ml ampcilline-containing super broth (a culture medium obtained by mixing A solution and B solution; A solution being prepared by dissolving bactotryptone 12 g, yeast extract 24 g, and glycerol 5 ml in water to make the total amount 900 ml, followed by autoclave, and B solution being prepared by dissolving potassium dihydrogenphosphate 3.81 g, and dipotassium hydrogenphosphate 12.5 g in water to make the total amount 100 ml, followed by autoclave) in a ratio of 9:1 (v/v), and the plasmid DNA was extracted and purified in a large amount by alkali-SDS method. The plasmid comprising the AOX2 promoter region was named pMM030 (FIG. 3) and the plasmid comprising the AOX2 structural gene and terminator was named pMM031 (FIG. 4). The size of the fragments produced by the digestion of these plasmids with various restriction enzymes showed the same pattern as had been reported.

EXAMPLE 2

Determination of nucleotide sequence of AOX2 promoter region

The plasmid vector pMM030 obtained in Example 1 was digested with EcoRI. The obtained 1.5 kb fragment was recovered, and the DNA fragment was treated with a DNA blunting kit (manufactured by Takara Shuzo Kabushiki Kaisha) to give a DNA fragment having blunt ends.

On the other hand, plasmid pUC19 was digested with XbaI, treated with Mung Bean Nuclease (manufactured by Takara Shuzo Kabushiki Kaisha), and treated with alkali phosphatase, followed by ligation of the DNA fragment obtained above with the XbaI cleavage site. By these procedures, plasmids wherein AOX2 promoter region DNA was subcloned to the XbaI site of pUC19 were obtained.

These plasmids were treated using a deletion kit for Kilo-Sequence (manufactured by Takara Shuzo Kabushiki Kaisha) to prepare 5 or 6 clones of deletion mutants having an insertion size varying by 150 to 300 bp. The nucleotide sequence of these deletion mutants was identified using M13 dideoxy sequencing kit (manufactured by Takara Shuzo Kabushiki Kaisha). As a result, the entire nucleotide sequence for 1.5 kb upstream from ATG of the AOX2 structural gene was identified.

EXAMPLE 3

Figure 5:
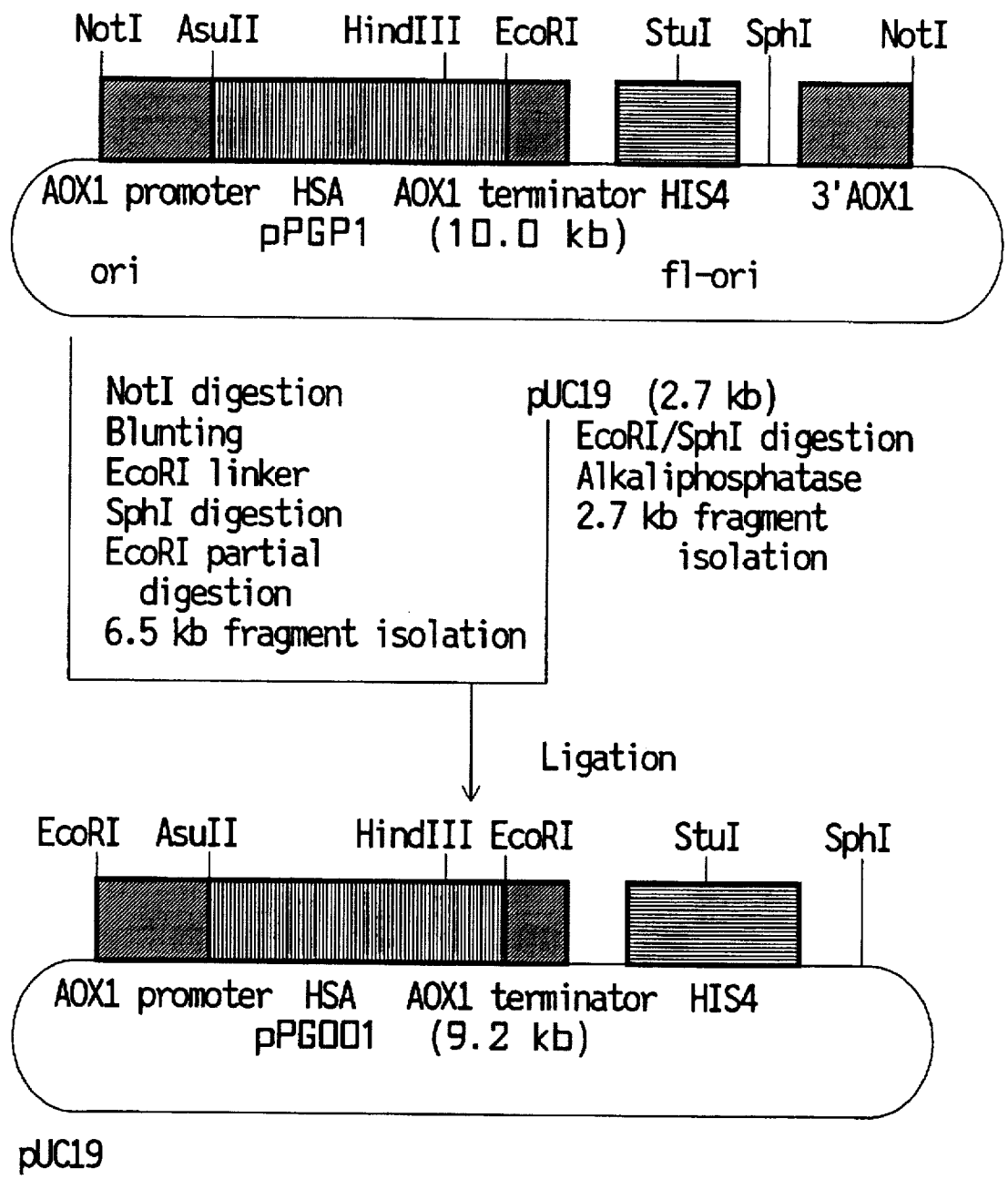
FIG. 5 depicts the construction of pPG001.
Figure 6:
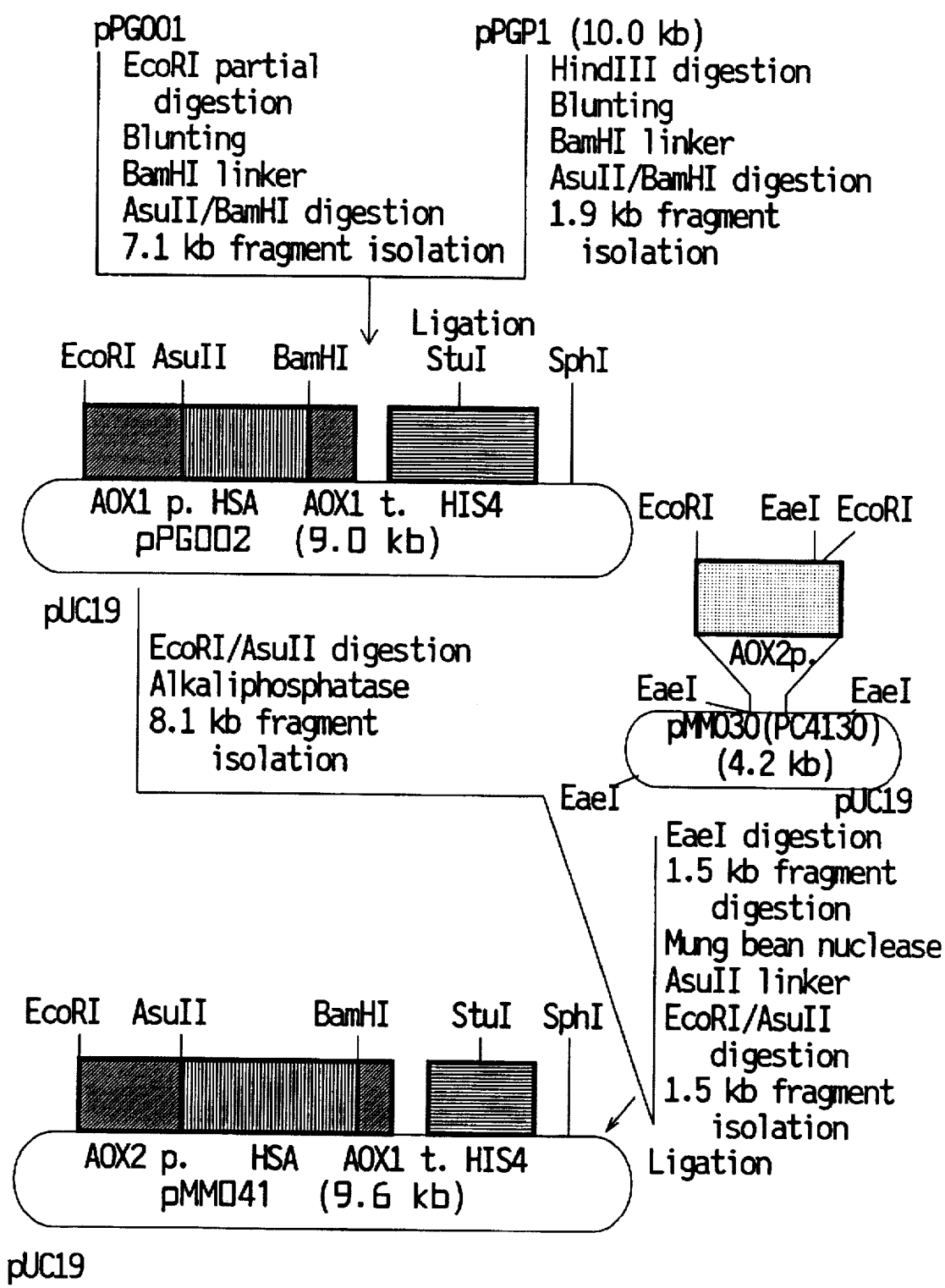
FIG. 6 depicts the construction of pMM041 where HSA is expressed under the control of AOX2 promoter. In the Figure, t. means terminator and p. means promoter.
Figure 7:
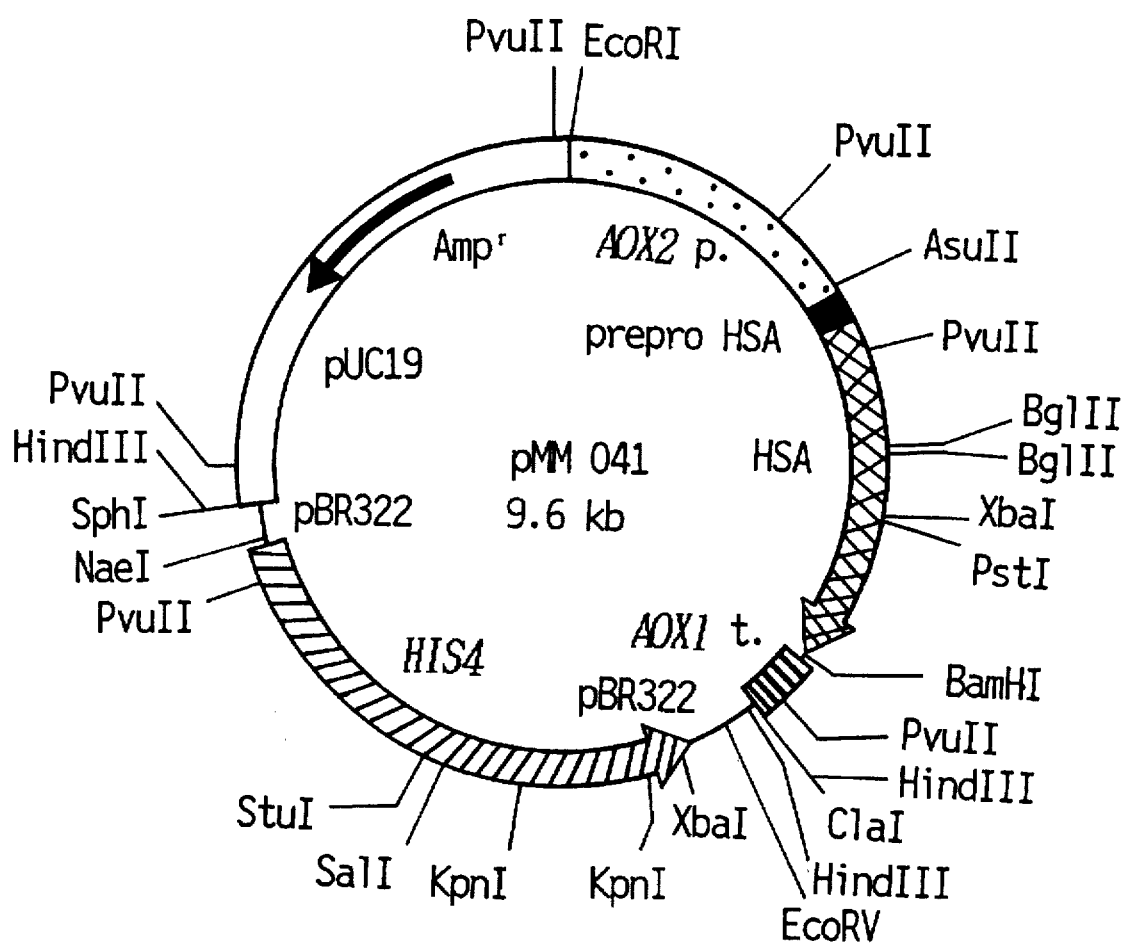
FIG. 7 shows a restriction enzyme map of an HSA expression vector pMM041, wherein AOX2 p. is AOX2 promoter, AOX1 t. is AOX1 terminator, prepro HSA is prepro HSA sequence, HSA is HSA cDNA, HIS4 is *P. pastoris* HIS4 gene, Amp$^r$ is ampicillin-resistant gene, pUC19 is pUC19-derived sequence, and pBR322 is pBR322-derived sequence.

Construction of HSA expression vector controlled by AOX2 promoter pPGP1 was digested with NotI, and blunted using a DNA blunting kit (manufactured by Takara Shuzo Kabushiki Kaisha). Thereto was ligated EcoRI linker d(pG-G-A-A-T-T-C-C) (manufactured by Takara Shuzo Kabushiki Kaisha). A complete digestion with SphI and partial digestion with EcoRI were conducted, and 6.5 kb DNA fragment was recovered and purified. pUC19 was digested with EcoRI and SphI, subjected to alkali phosphatase treatment, and ligated with the above-mentioned fragment. Thus, a pUC19-derived plasmid pPG001 having HIS4 as a selection marker wherein HSA was expressed under the control of AOX1 promoter was obtained (FIG. 5). pPG001 was partially digested with EcoRI and blunted with a DNA blunting kit (manufactured by Takara Shuzo Kabushiki Kaisha). On the other hand, a BamHI linker having a sequence of GGGATCCC was synthesized by phosphoamidite method using a DNA synthesizer Model 381A (manufactured by Applied Biosystem), which was then phosphorylated with T4 polynucleotide kinase (manufactured by Takara Shuzo Kabushiki Kaisha) and ligated with the fragment of pPG001 previously blunted as described. Then, it was digested with AsuII and BamHI, and a 7.1 kb fragment was purified. Meanwhile, pPGP1 was digested with HindIII, and blunted using a DNA blunting kit (manufactured by Takara Shuzo Kabushiki Kaisha), there-with ligated was BamHI linker d(pG-G-G-A-T-C-C-C) (manufactured by Takara Shuzo Kabushiki Kaisha). It was digested with AsuII and BamHI, and a 1.9 kb fragment was purified, with which the above-mentioned 7.1 kb fragment was ligated to give pPG002 (FIG. 6).

pMM030 was digested with EaeI and a 1.5 kb fragment was recovered. It was blunted by Mung Bean Nuclease treatment (manufactured by Takara Shuzo Kabushiki Kaisha). Then, using a DNA synthesizer Model 381A (manufactured by Applied Biosystem), AsuII linker having a sequence of CTTCGAAG was synthesized by phosphoamidite method. The AsuII linker was phosphorylated with T4 polynucleotide kinase (manufactured by Takara Shuzo Kabushiki Kaisha) and ligated with the fragment of pMM030 previously blunted as described. Then, it was digested with gcoRI and AsuII, and a 1.5 kb AOX2 promoter fragment was recovered. Meanwhile, plasmid pPG002 having an HIS4 region wherein HSA expressed under the control of AOX1 promoter was digested with EcoRI and AsuII, and an 8.1 kb fragment lacking AOXI promoter region was treated with alkali phosphatase and recovered, after which it was ligated with the AOX2 promoter region 1.5 kb fragment to prepare a plasmid pMM041 which allows expression of HSA under the control of AOX2 promoter (FIG. 6). The restriction enzyme map of pMM041 is shown in FIG. 7.

EXAMPLE 4

Amplification of AOX2 promoter gene which has undergone deletion of 5' upstream region, by PCR method In order to amplify by PCR method, using AOX2 promoter fragments having a length of an upstream region from the translation initiation codon ATG, of 803 bp, 462 bp, 341 bp, 273 bp or 214 bp, the primer sequence with an EcoRI site at the 5' terminal or an AsuII site at the 3' terminal was designed, synthesized using a 392 type DNA/RNA synthesizer (manufactured by Applied Biosystem) by phosphoamidite method, and purified by an NAP 10 column (manufactured by Pharmacia). The respective sequences are given in Table 1 as SEQ ID NOS: 4–9, respectively.

TABLE 1

| Primer | nucleotide sequence | plus strand or reverse strand |
|---|---|---|
| PCR60 | 5'-GAATTCACTAAGCGAGTCATCATC-3' | plus |
| PCR65 | 5'-GAATTCCAGCTGTCAGCTACCTAG-3' | plus |
| PCR71 | 5'-GAATTCCCAAGTAGGCTATTTTTG-3' | plus |
| PCR66 | 5'-GAATTCTACAGAAGCGTCCTACCC-3' | plus |
| PCR68 | 5'-GAATTCCGATTATTGGTATAAAAG-3' | plus |
| PCRRV | 5'-TTCGAAGTTTTTCTCAGTTGATTT-3' | reverse |

Using any of the plus strands and the reverse strand primer PCRRV, PCR was performed with Pichia pastoris chromosome DNA. The PCR apparatus was Perkinelmer DNA thermalcycler (manufactured by CETUS CORPORATION) and the reagent was Gene Amp™ DNA amplification kit (manufactured by Takara Shuzo Kabushiki Kaisha). Low molecule substances present in a reaction mixture were removed by Ultrafree C3TK (manufactured by Millipore), and the resulting mixture was used as a purified PCR product.

EXAMPLE 5

Figure 8:
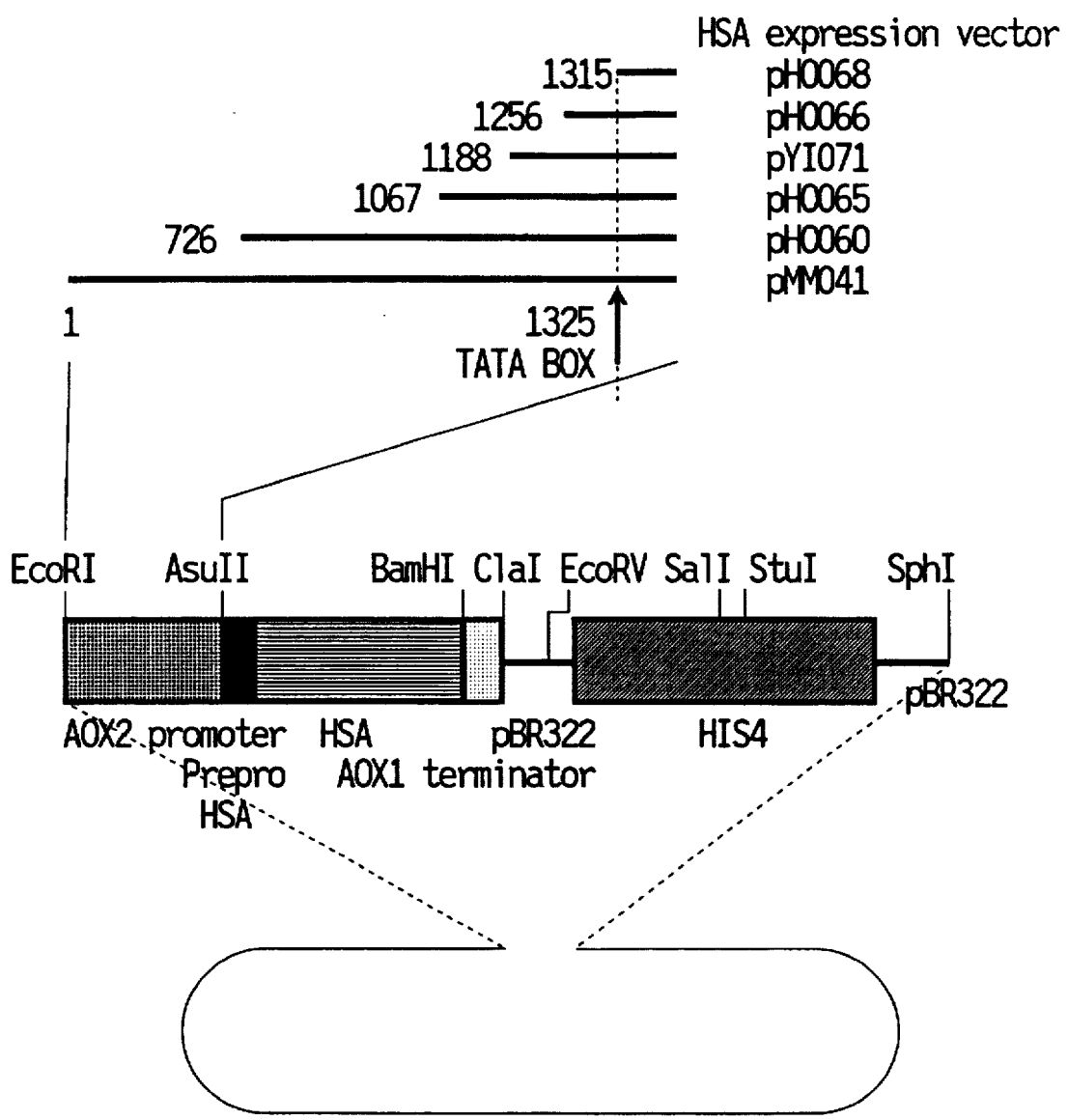
FIG. 8 shows an HSA expression vector controlled by an upstream-deleted AOX2 promoter.

Construction of HSA expression vector controlled by upstream-deleted AOX2 promoter An HSA expression vector pMM041 was double-digested with EcoRI and AsuII; natural AOX2 promoter was separated and removed by agarose gel electrophoresis; and the purified PCR product which was double-digested with EcoRI and AsuII, as obtained in Example 4 was inserted in the vector portion, whereby to produce a plasmid containing a 5'-deleted AOX2 promoter. So as to confirm that the inserted DNA fragment was an AOX2 promoter gene which underwent deletion of 5'-upstream region, the nucleotide sequence was determined by dideoxy method using a fluorescence primer by ALF. DNA sequencer (manufactured by Pharmacia). The fluorescence primer used was Universal primer (manufactured by Pharmacia) and the reaction kit used was Auto read sequencing kit (manufactured by Pharmacia). As a result, the plasmids prepared were, as originally designed, all confirmed to be HSA expression vectors controlled by 5'-deleted AOX2 promoter. The HSA expression vector obtained using a primer PCR60 and having an upstream region length from ATG of 803 bp (nucleotide number of 5' endpoint of promoter being 726) was named pHO060; the one obtained using a primer PCR65 and having an upstream region length from ATG of 462 bp (nucleotide number of 5' endpoint of promoter being 1067) was named pHO065; the one obtained using a primer PCR71 and having an upstream region length from ATG of 341 bp (nucleotide number of 5' endpoint of promoter being 1188) was named pYI071; the one obtained using a primer PCR66 and having an upstream region length from ATG of 273 bp (nucleotide number of 5' endpoint of promoter being 1256) was named pHO066; and the one obtained using a primer PCR68 and having an upstream region length from ATG of 214 bp (nucleotide number of 5' endpoint of promoter being 1315) was named pHO068 (FIG. 8).

EXAMPLE 6

Construction of HSA expression vector pHO090 and pHO095

Two kinds of site-directed mutation were introduced into regions in nucleotides 1188–1212 of AOX2 promoter by utilizing PCR method, and the influence of the mutation on the transcription activity of the promoter was analyzed.

The introduction of the site-directed mutation by utilizing PCR method followed the method described in a literature (Ito, W., et al, Gene, 102, 67–70, 1991). As the template plasmid, used was plasmid pHO074 obtained by cleaving an AOX2 promoter and about 1.2 kb of the 5'-region of HSA from HSA expression vector pHO065 with EcoRI and PstI, and subcloning same to EcoRI/Pst I site of cloning vector pUC19. Then, two kinds of primers, UASps, for site-directed mutagenesis were synthesized. The sequences thereof are given in FIG. 9, and the steps for introducing the mutation are summarized in FIG. 10 and FIG. 11. First, each PCR product was prepared using a UASp and a primer RV complementary to the 3' sequence of multicloning site (manufactured by Takara Shuzo Kabushiki Kaisha). In addition, PCR products were prepared, in other reaction tubes, using primer M4 (manufactured by Takara Shuzo Kabushiki Kaisha) complementary to the 5' sequence of the multicloning site, and primer MUTF3 (manufactured by Takara Shuzo Kabushiki Kaisha) which was complementary to the 3' sequence of the multicloning site but the sites corresponding to the SphI site and HindIII site of the multicloning site had been deleted by nucleotide replacement. The latter PCR products underwent deletion of the sites corresponding to the SphI site and HindIII site of the multicloning site. After removing low molecular substances from the both PCR products, equivalent amounts of the both products were mixed, denatured with heat and cooled for annealing, thereby forming heteroduplexes. The heteroduplexes were completed by polymerase reaction, and a second PCR was conducted using M4 and RV. By this process, two kinds of PCR products can be theoretically obtained, i.e. desired UAS into which mutation has been introduced and one with the sites corresponding to the SphI site and HindIII site of the multicloning sites having been eliminated. Accordingly, the UAS alone into which mutation has been introduced can be obtained by digesting the mixture with EcoRI and SphI and recloning same to EcoRI/SphI of pUC19 upon removal of low molecular substances. The nucleotide sequence of the AOX2 promoters of several kinds of plasmids thus obtained was determined, and AOX2 promoters into which site-directed mutation had been introduced were obtained. The plasmids carrying those were named pHO086 and pHO087.

Figure 12:
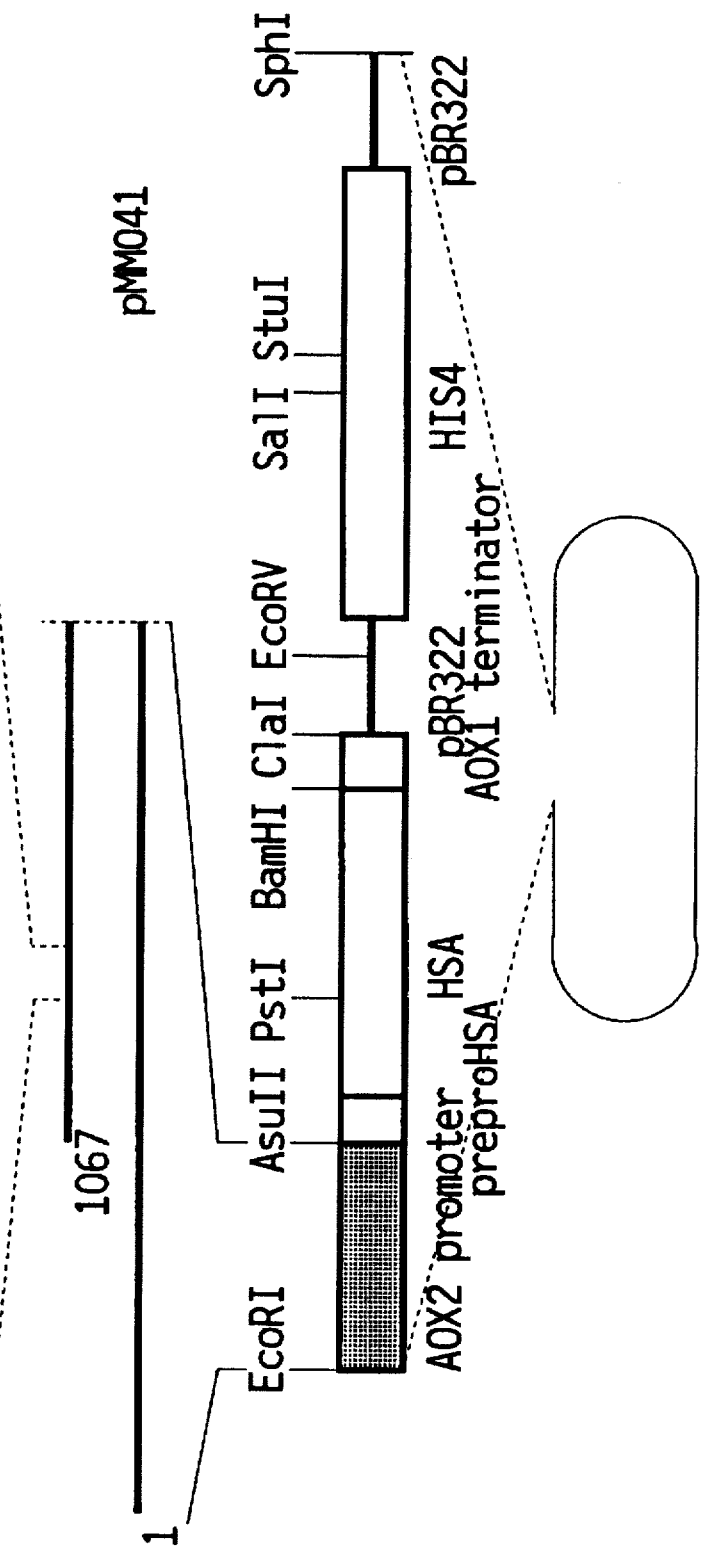
FIG. 12 depicts three HSA expression vectors: pHO090 which contains SEQ ID NO:18 having a mutant UAS region; pHO095 which contains SEQ ID NO:19 having a mutant UAS region; and pHO065 which contains the wild-type UAS region of SEQ ID NO:1, nucleotides 1170–1219.

The pHO086 and pHO087 were digested with EcoRI and Pst I to give fragments containing a 462 bp AOX2 promoter and about 1.2 kb of 5' region of HSA gene. By exchanging the fragment with about 1170 bp fragment including natural AOX2 promoter and 5' region of HSA gene, which was obtained by digesting HSA expression vector pMM041 with EcoRI and PstI, constructed were HSA expression vectors pHO090 and pHO095 which were under the control of the site-directedly mutated promoters (FIG. 12).

EXAMPLE 7

Obtainment of AOX2 promoter having mutated URS2 region (nucleotides 1274–1314) and HSA expression vector carrying said promoter By subculturing a *Pichia pastoris* strain showing poor methanol utilization due to the deletion of the AOX1 gene, in a medium containing methanol as a sole carbon source, a mutant strain showing the growth improved as well as a strain having an AOX1 gene can be obtained. It has been made clear that the mutation occurred in AOX2 promoter results in an improved transcription activity, which in turn causes an improved growth (Japanese Patent Application No. 63598/1991). Using this method, a mutant strain improved in methanol utilization was obtained from an AOX1-deleted strain. PC4105 strain which is an AOX1-deleted strain was successively subcultured in YPM medium containing methanol as a sole carbon source. The subculture was spread on a YNB w/o a.a. —MeOH agar medium (0.67% yeast nitrogen base without amino acids, 2% methanol, 1.5% agar) at $10^7$–$10^8$ cell/agar medium. The AOX1 deletion strain showed remarkably slow growth, whereas the growth of the mutant strain was fast to the degree that it formed colonies in 3 or 4 days. In this way, mutant strains showing enhanced methanol utilization were obtained from cells subcultured for 20–45 generations, and named SHG4105-4 stain and SHG4105-8 strain.

The AOX2 promoter of the obtained mutant strain was cloned by utilizing PCR method. That is, PCR was performed with the chromosome DNAs of the mutant strain and PC4105 strain using, as a plus strand primer, a DNA fragment (5'-CCGGATCCACTAAGCGAGTCATCATC-3') (SEQ ID NO:10) with BamHI site at the 5'-terminal to hybridize to nucleotides 726–743 of AOX2 promoter, and using, as a reverse strand primer, a DNA fragment (5'-CCGAATTCGACAATATTCTTTGATGC-3') (SEQ ID NO:11) with EcoRI site at the 5' terminal to hybridize to nucleotides 1386–1369. The AOX2 promoter fragments amplified as described were cloned into BamHI/EcoRI site of pUC19.

Then, the nucleotide sequence of the AOX2 promoter fragment on the cloning vector was determined. In the parent PC4105 strain, the nucleotide sequence of AOX2 promoter was completely intact. In SHG4105-4 strain, T (1274) of natural AOX2 promoter was replaced with C. In SHG4105-8 strain, T (1274) of natural AOX2 promoter was maintained, but nucleotides 1296–1314 were duplicated once.

Figure 13A:
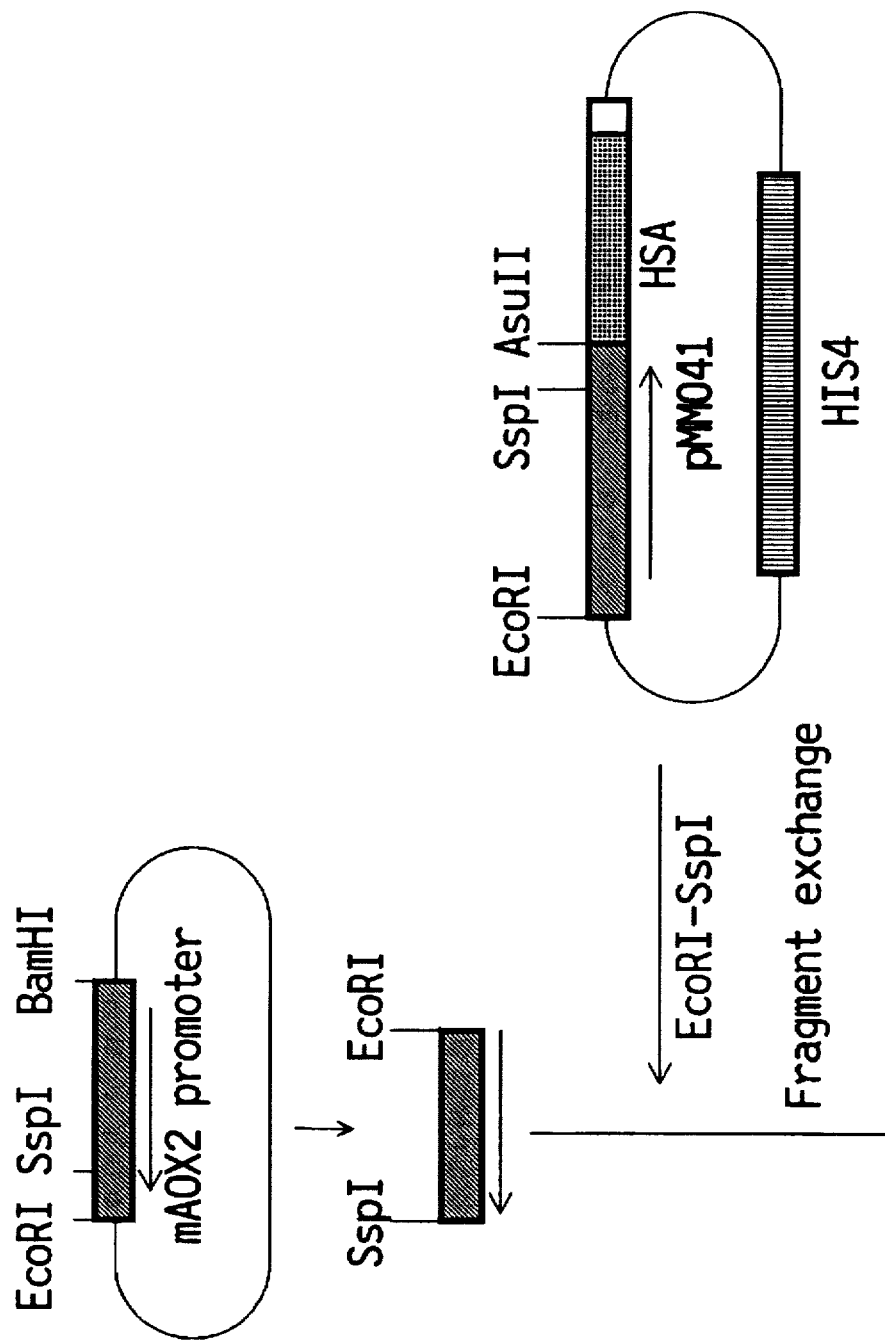
FIG. 13 shows the construction of an HSA expression vector under the control of an AOX2 promoter having mutation in URS2 (nucleotides 1274–1314 of Sequence Listing, Sequence No. 1).
Figure 13B:
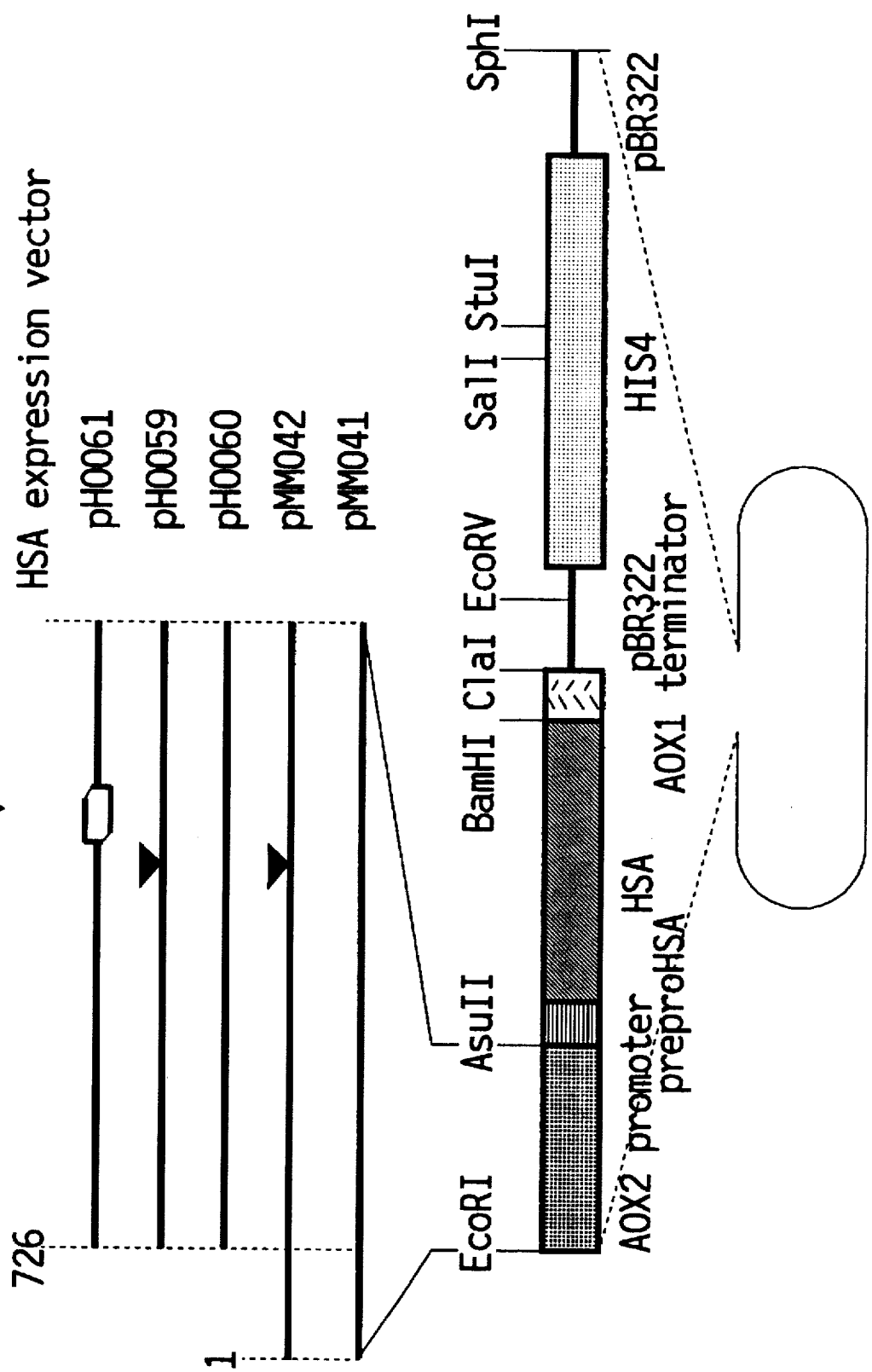

Vectors allowing HSA expression under the control of the cloned mutant AOX2 promoters were constructed. First, BamHI site at the 5' terminal of a mutant AOX2 promoter was converted to EcoRI site, and the mutant AOX2 promoter fragments were isolated with EcoRI-SspI. Then, natural AOX2 promoter in HSA expression vector pMM041 was replaced with the mutant AOX2 promoter to give vectors pHO059 (point mutation) and pHO061 (duplication mutation) capable of HSA expression under the control of mutant AOX2 promoter (FIG. 13).

EXAMPLE 8

Figure 14:
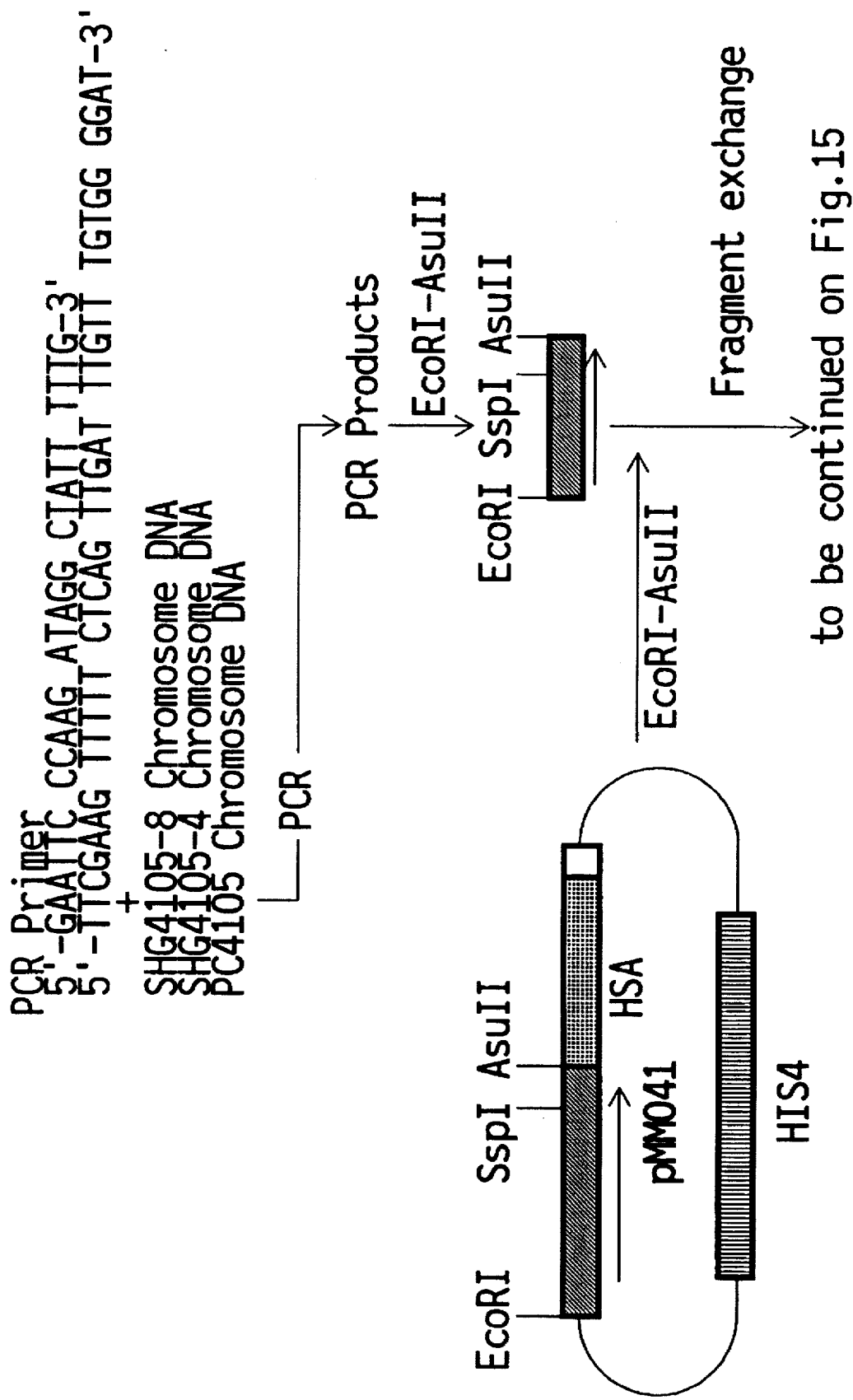
FIG. 14 shows the construction of an HSA expression vector under the control of an AOX2 promoter wherein URS1 has been deleted and URS2 has been mutated using PCR primers, SEQ ID NOS:20 and 21.
Figure 15:
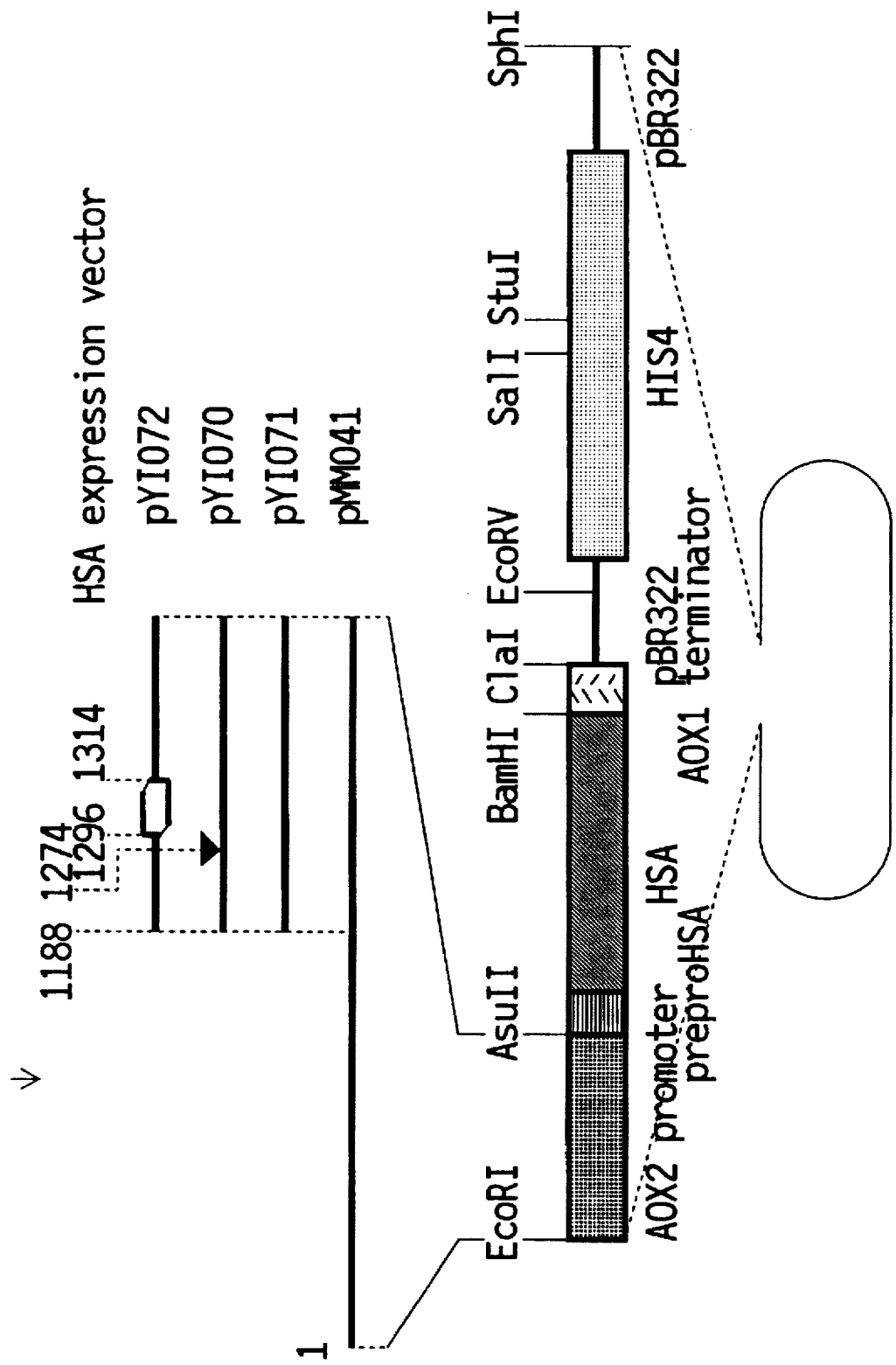
FIG. 15 shows the construction of an HSA expression vector under the control of an AOX2 promoter wherein URS1 has been deleted and URS2 has been mutated.

Obtainment of AOX2 promoter lacking URS1 but having mutant URS2 and HSA expression vector carrying said promoter Chromosome DNAs of SHG4105-4 strain having an AOX2 promoter which underwent point mutation at nucleotide 1274, SHG4105-8 strain having a duplication mutation of nucleotides 1296–1314, and GTS115 strain having natural AOX2 promoter were respectively subjected to PCR using, as a plus strand primer, a DNA fragment (5'-GAATTCCCAAGATAGGCTATTTTTG-3') (SEQ ID NO:12) with EcoRI site at the 5' terminal to hybridize to nucleotides 1188–1206 of AOX2 promoter, and using, as a reverse strand primer, a DNA fragment (5'-TTCGAAGTTTTTCTCAGTTGATTTGTTTGTGGGAT-3') (SEQ ID NO:13) with AsuII site at the 5' terminal to hybridize to nucleotides 1529–1501. Since the DNA fragments amplified as described do not have a region extending upstream from nucleotide 1187 inclusive, they lack URS1, but maintain UAS. After digestion of the DNA fragments with EcoRI and AsuII, natural AOX2 promoter of HSA expression vector pMM041 was replaced with them to give vectors pYI070 (point mutation), pYI072 (duplication mutation), and pYI071 (natural type) (FIGS. 14 and 15).

EXAMPLE 9

Figure 17:
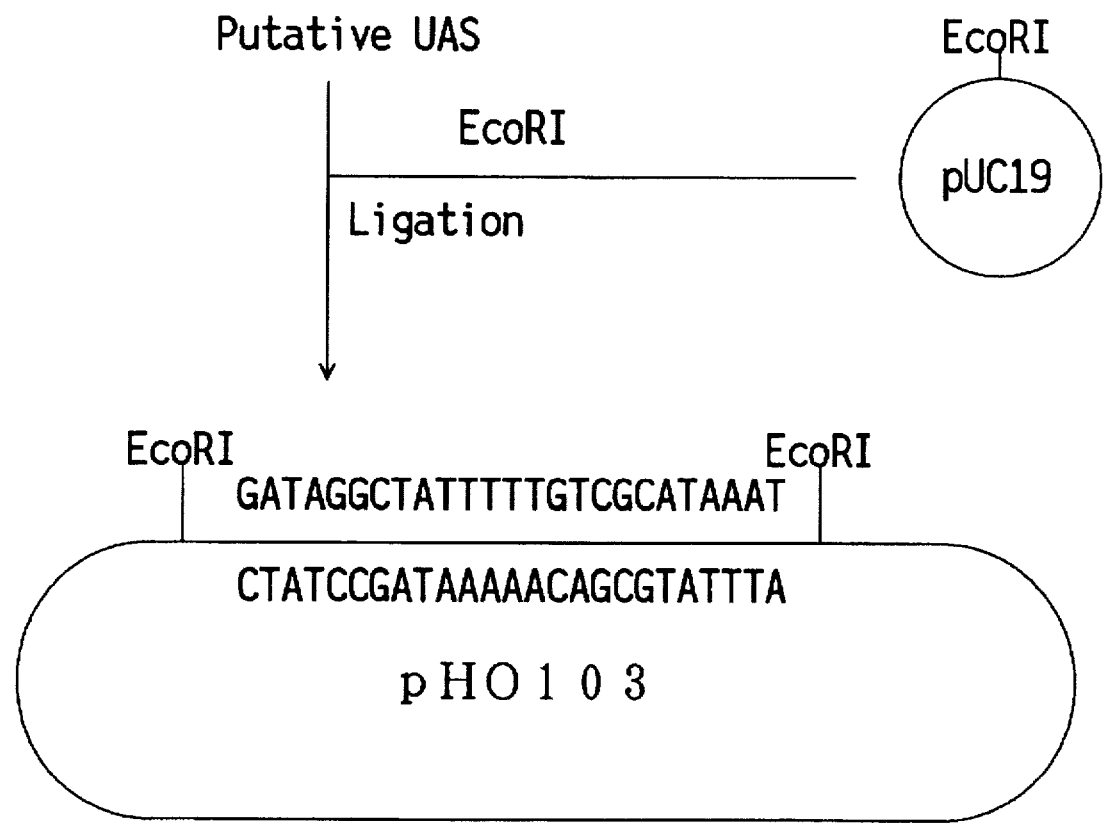
FIG. 17 shows the construction of a plasmid pHO103 having a synthetic DNA fragment, SEQ ID NO:14, having a nucleotide sequence 1192–1216 of Sequence Listing, Sequence No. 1, which is a putative USA sequence.

Synthesis and subcloning of oligonucleotide (I) and construction of HSA expression vector having said nucleotides A homology search in the nucleotide sequences of AOX1 promoter to the AOX2 promoter was conducted to find two homologous sequences (FIG. 16). Based on the result, the function of the region including putative UAS in the AOX2 promoter, i.e. nucleotides 1192–1216, 5'-GATAGGCTATTTTTGTCGCATAAAT-3' (SEQ ID NO:2), was investigated. That is, a sequence wherein EcoRI sites were added to the both ends of the 25 bp fragment of nucleotides 1192–1216 was chemically synthesized using a DNA/RNA synthesizer (Model 392, manufactured by ABI). The sequences were: plus strand, 5'-AATTCGATAGGCTATTTTTGTCGCATAAATG-3' (SEQ ID NO:14), and reverse strand, 5'-AATTCATTTATGCGACAAAAATAGCCTATCG-3' (SEQ ID NO:15). After synthesis, they were purified with an NAP10 column (manufactured by Pharmacia). About 5 µg each of the plus strand nucleotide and the reverse nucleotide were mixed, heated at 95° C. for 5 minutes, and cooled for annealing. After the annealing, it was subcloned to the EcoRI site of pUC19. The plasmid was named pHO103. The construction thereof is shown in FIG. 17.

The HSA expression vectors pHO060, pHO066, pHO068 and pYI071 obtained in Example 5, the HSA expression vectors pHO090 and pHO095 obtained in Example 6 and having partially mutant UAS regions, the HSA expression vectors pHO059 and pHO061 obtained in Example 7, and the HSA expression vectors pYI070, pYI072 and pYI071 obtained in Example 8 were respectively digested with gcoRI. The linear fragment and the aforementioned annealed synthetic DNA fragment [oligonucleotide (I)] were ligated. Using the ligated fragments, E. coli JM109 was transformed. Plasmids were prepared from several transformants and the plasmids having inserted fragment at the EcoRI site were selected by restriction enzyme analysis and DNA sequencing. Then, the copy number and the direction of the synthetic DNA sequence fragment inserted therein were determined by DNA sequencing. As a result, HSA expression vectors having 1 to 3 synthetic sequences inserted in an upstream from various AOX2 promoters were obtained by screening. The structure in part of the promoter carried by the vectors obtained are shown in FIGS. 18 and 19.

Figure 18:
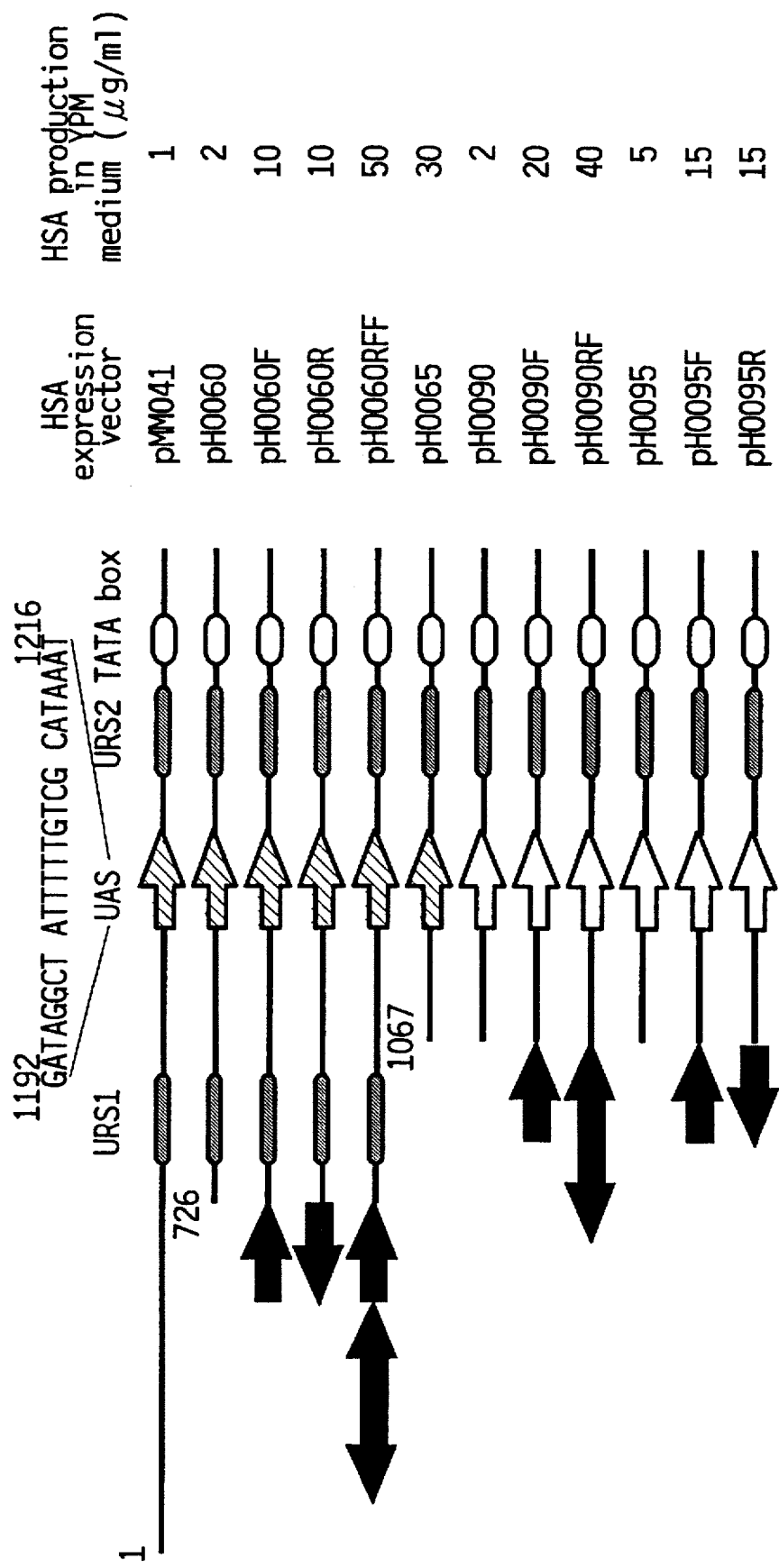
FIG. 18 shows the structure of a mutant AOX2 promoter having a synthetic DNA fragment putatively having UAS sequence at the 5' end and HSA produced thereby, wherein hatched arrow indicates wild-type UAS, SEQ ID NO:2, black arrow indicates synthesized UAS and white arrow indicates mutated UAS (to be continued on FIG. 19).

Note that in FIGS. 18 and 19, the HSA expression vector having the synthetic DNA sequence fragment inserted in the upstream from the AOX2 promoter in the forward direction is indicated with an F added as an suffix to the name of the HSA expression vector and with an R when it is inserted in the reverse direction.

EXAMPLE 10

Obtainment of single copy transformant

The constructed HSA expression vector was digested with StuI to adjust to 1 μg/μl, which was then integrated into the HIS4 region of the host P. pastoris GTS115 strain and a transformant was prepared therefrom by the use of ALKA-LICATION Yeast Transformation Kit (Bio101) and a lithium acetate method. A suitable number of colonies were taken from each plasmid and spread on an SD w/o a.a. plate which was used as a preservation plate. The transformant was replicated on a YPM agar medium (1% yeast extract, 2% peptone, 2% methanol, 1.5% agar) with a nitrocellulose membrane placed thereon and cultured for 72 hours. Then, the secreted HSA which was trapped by the nitrocellulose membrane was qualitatively assayed by immunobloting using an anti-HSA antibody, whereby primary screening of HSA-producing strains was done. DNA was extracted from several HSA producing strains per each plasmid and digested with BglII. The digested DNA fragments were subjected to agarose gel electrophoresis and the separated fragment was transferred onto a nylon membrane, which was then analyzed by southern blotting with the use of HSAcDNA fragment as a probe. A transformant confirmed to have a DNA which migrated as a 4.5 kb single band in electrophoresis was taken as a transformant into which a single copy of plasmid had been integrated.

The function of the synthesized DNA sequences was examined based on the HSA production by these single copy transformants as an index.

Culture of the single copy transformant was carried out as follows. First, a preculture was done for 1 to 3 days in 2 ml of YPD (1% yeast extract, 2% peptone, 2% glucose) medium/test tube at 29.5° C. and 170 rpm. The obtained preculture was inoculated to 3 ml of YPM (YP-2% methanol) medium/test tube in such a manner that made the OD 540 nm at the time of inoculating 0.1 and cultured at 29.5° C. and 170 rpm for 72 hours. The HSA production in the supernatant at 72 hours of culture was determined by the RPHA method. The results are shown in FIGS. 18 and 19.

The pHO060 transformant showed 2 μg/ml HSA production. In contrast, the transformant transformed with a plasmid pHO060F wherein a synthetic DNA fragment had been inserted in AOX2 promoter at 5' upstream (further upstream from URS1) of pHO060 in the forward direction showed 5 times greater HSA production (10 μg/ml). The increase in the HSA production by the pHO060F transformant was speculated to be attributable to the inserted synthetic DNA fragment. In a similar manner, the transformant transformed with a plasmid pHO060R wherein a synthetic DNA fragment had been inserted in the reverse direction showed 10 μg/ml of HSA production, which indicates absence of a relation between the transcription enhancing activity and the direction of the insertion. The pHO060RFF transformant inserted with 3 copies of the synthetic DNA fragments in the directions of reverse, forward and forward in order from the 5' end produced 50 μg/ml of HSA, 25 times greater production than did pHO060 transformant.

The HSA production-enhancing activity due to a pHO060-derived plasmid was also acknowledged in pYI071, pHO066 or pHO068-derived plasmid transformant. Accordingly, it was found that the synthetic DNA fragment functioned as "UAS" and the function was still more enhanced by the insertion of multicopies. The plasmid inclusive of pHO068F obtained by inserting synthetic DNA fragment into pHO068 presumably includes UAS and TATA box only as the promoter elements. What is more, UAS is located near the 5' end from the TATA box. Notwithstanding such fact, the plasmid tranformants showed sufficient HSA production induced by methanol. In other words, the important elements to act as a promoter are USA and TATA box alone.

The function of the synthetic DNA fragment as a USA was also acknowledged when the fragment was inserted into the 5' end of the AOX promoters of pHO090 and pHO095. That is, in the case of pHO090 and pHO095, the original UAS underwent site-directed mutation to lose most of its function, whereas the insertion of the synthetic DNA fragment resulted in the recovery of the function.

Based on the foregoing results, it was found that the synthetic DNA fragment reinforced the transcription activity of a promoter in a copy number-dependent manner. There was found no relation between the direction of insertion and the reinforcing activity. In addition, the insertion at optional site upstream from the 5' end of TATA box resulted in a reinforcing effect. The results indicate that the synthetic DNA fragment suffices for use as a HAS for a yeast. It was clarified that the 25 bp synthetic DNA fragment contained complete UAS of AOX2 promoter.

EXAMPLE 11

Glucose repression of mutant AOX2 promoter

All Pichia strains which express HSA under the control of the mutant AOX2 promoter of the present invention were cultured in YPM, YPD or YPDM medium and the transcription regulation by the promoters was analyzed with the HSA expression as an index. Preculture was done for 1 to 3 days in 2 ml of YPD (1% yeast extract, 2% peptone, 2% glucose) medium/test tube at 29.5° C. and 170 rpm. The obtained preculture was inoculated to 3 ml of YPM (YP-2% methanol) medium/test tube, YPD medium/test tube and YPDM (YP-2% glucose, 2% methanol) medium/test tube in such a manner that made the OD 540 nm at the time of inoculating 0.1 and cultured at 29.5° C. and 170 rpm for 96 hours. The HSA production was determined by the RPHA method.

The cell proliferation and HSA production in the supernatant were examined with regard to the all cells in the three kinds of media. The HSA production at 48 hours of culture in the late period of logarithmic growth phase is shown in Table 2 and Table 3 along with the presence or absence of promoter transcription regulatory element URS1, UAS or URS2. The HSA production at 72 hours of culture in the stationary phase is shown in Table 4 and Table 5 along with the presence or absence of promoter transcription regulatory element. In the Tables, − is a deleted element, + is a natural-type element, ⊕ is an artificially added element, SM is a site-directed mutation in element, PM is a point mutation (change of 1274th T to C) in element and DM is a duplicate mutation (1294th–1314th nucleotides) in element.

TABLE 2

HSA production at 48 hours - 1

| Plasmid | Regulatory elements | | | HSA production at 48 hr (µg/ml) | | |
|---|---|---|---|---|---|---|
| | URS1 | UAS | URS2 | YPM | YPD | YPDM |
| pMM041 | + | + | + | 0.5 | 0.01 | 0.01 |
| pMM042 | + | + | PM | 30 | 0.1 | 0.05 |
| pHO061 | + | + | DM | 20 | 0.1 | 0.1 |
| pHO060 | + | + | + | 1 | 0.05 | 0.02 |
| pHO060F | + | ⊕+ | + | 3 | 0.07 | 0.05 |
| pHO060R | + | ⊕+ | + | 5 | 0.1 | 0.05 |
| pHO060RFF | + | ⊕⊕+ | + | 30 | 0.07 | 0.07 |
| pHO073 | − | + | + | 7 | 0.2 | 0.3 |
| pHO076 | − | + | + | 7 | 0.2 | 0.3 |
| pHO064 | − | + | + | 7 | 0.3 | 0.5 |
| pHO065 | − | + | + | 15 | 2 | 2 |
| pHO088 | − | SM | + | 0.5 | 0.7 | 0.7 |
| pHO089 | − | SM | + | 2 | 0.7 | 0.7 |
| pHO090 | − | SM | + | 1 | 2 | 2 |
| pHO090F | − | ⊕SM | + | 10 | 1 | 0.7 |
| pHO090RF | − | ⊕SM | + | 20 | 0.3 | 0.5 |
| pHO091 | − | SM | + | 2 | 1 | 1 |
| pHO095 | − | SM | + | 3 | 0.5 | 0.5 |
| pHO095F | − | ⊕SM | + | 7 | 0.5 | 0.5 |
| pHO095R | − | ⊕SM | + | 7 | 0.5 | 0.5 |

TABLE 3

HSA production at 48 hours - 2

| Plasmid | Regulatory elements | | | HSA production at 48 hr (µg/ml) | | |
|---|---|---|---|---|---|---|
| | URS1 | UAS | URS2 | YPM | YPD | YPDM |
| pYI071 | − | + | + | 20 | 1 | 1 |
| pYI071F | − | ⊕+ | + | 40 | 1.5 | 1 |
| pYI071R | − | ⊕+ | + | 50 | 1.5 | 2 |
| pYI071FRF | − | ⊕⊕⊕+ | + | 50 | 1.5 | 1.5 |
| pYI070 | − | + | PM | 50 | 5 | 2 |
| pYI072 | − | + | DM | 50 | 1 | 1 |
| pHO080 | − | − | + | 0.3 | 0.5 | 0.3 |
| pHO066 | − | − | + | 0.3 | 0.5 | 0.5 |
| pHO066R | − | ⊕ | + | 40 | 0.3 | 1 |
| pHO066FR | − | ⊕+ | + | 75 | 0.5 | 0.7 |
| pHO068 | − | − | − | 1 | 4 | 3 |
| pHO068F | − | ⊕ | − | 30 | 5 | 3 |
| pHO068R | − | ⊕ | − | 30 | 3 | 2 |
| pHO068FF | − | ⊕⊕ | − | 70 | 5 | 5 |
| pHO068FR | − | ⊕⊕ | − | 60 | 2 | 3 |
| pHO068FRR | − | ⊕⊕⊕ | − | 60 | 2 | 2 |

TABLE 4

HSA production at 72 hours - 1

| Plasmid | Regulatory elements | | | HSA production at 72 hr (µg/ml) | | |
|---|---|---|---|---|---|---|
| | URS1 | UAS | URS2 | YPM | YPD | YPDM |
| pMM041 | + | + | + | 1 | 0.5 | 0.3 |
| pMM042 | + | + | PM | 60 | 1 | 30 |
| pHO061 | + | + | DM | 50 | 1 | 20 |
| pHO060 | + | + | + | 2 | 1 | 1 |
| pHO060F | + | ⊕+ | + | 10 | 1.5 | 5 |
| pHO060R | + | ⊕+ | + | 10 | 1 | 5 |
| pHO060RFF | + | ⊕⊕+ | + | 50 | 3 | 10 |
| pHO073 | − | + | + | 15 | 1 | 2.5 |
| pHO076 | − | + | + | 15 | 0.7 | 2.5 |
| pHO064 | − | + | + | 20 | 0.7 | 2.5 |
| pHO065 | − | + | + | 30 | 3 | 7 |
| pHO088 | − | SM | + | 1 | 2 | 1 |
| pHO089 | − | SM | + | 3 | 1 | 3 |
| pHO090 | − | SM | + | 2 | 2 | 2 |
| pHO090F | − | ⊕SM | + | 20 | 1.5 | 7 |
| pHO090RF | − | ⊕SM | + | 40 | 1 | 10 |
| pHO091 | − | SM | + | 3 | 2 | 3 |
| pHO095 | − | SM | + | 5 | 0.7 | 1.5 |
| pHO095F | − | ⊕SM | + | 15 | 0.7 | 5 |
| pHO095R | − | ⊕SM | + | 15 | 0.7 | 5 |

TABLE 5

HSA production at 72 hours - 2

| Plasmid | Regulatory elements | | | HSA production at 72 hr (µg/ml) | | |
|---|---|---|---|---|---|---|
| | URS1 | UAS | URS2 | YPM | YPD | YPDM |
| pYI071 | − | + | + | 40 | 2 | 15 |
| pYI071F | − | ⊕+ | + | 80 | 2 | 20 |
| pYI071R | − | ⊕+ | + | 100 | 2 | 20 |
| pYI071FRF | − | ⊕⊕⊕+ | + | 100 | 2 | 40 |
| pYI070 | − | + | PM | 80 | 7 | 40 |
| pYI072 | − | + | DM | 80 | 1.5 | 30 |
| pHO080 | − | − | + | 0.5 | 0.7 | 0.5 |
| pHO066 | − | − | + | 1 | 1 | 1 |
| pHO066R | − | ⊕ | + | 80 | 1.5 | 15 |
| pHO066FR | − | ⊕+ | + | 120 | 1 | 40 |
| pHO068 | − | − | − | 2 | 5 | 5 |
| pHO068F | − | ⊕ | − | 50 | 7 | 20 |
| pHO068R | − | ⊕ | − | 50 | 5 | 20 |
| pHO068FF | − | ⊕⊕ | − | 100 | 7 | 40 |
| pHO068FR | − | ⊕⊕ | − | 100 | 5 | 40 |
| pHO068FRR | − | ⊕⊕⊕ | − | 120 | 5 | 50 |

As a result, when UAS functionable on AOX2 promoter was present, methanol induction of HSA expression and glucose catabolite repression inhibiting methanol-inducive HSA expression pending glucose consumption were found (in culture in YPDM medium, methanol-induced HSA production occurred after 72 hours of glucose consumption).

In promoters (pHO068F, pHO068R and other pHO068-derived plasmids) having UAS and TATA box alone as promoter transcription regulatory elements, methanol induction, glucose repression and sufficient transcription activity were found.

On the other hand, promoters lacking UAS or having mutant UAS showed no methanol induction and scarcely produced HSA. From the foregoing, it was suggested that methanol induced generation of transcription promoting factor which acted on UAS.

In view of the glucose catabolite repression in the case where UAS was present but other sequences were void (pHO068F), it was suggested that glucose preferentially blocked the route of transcription induction by methanol. Moreover, regulation of methanol and glucose, and the presence of URS1 or URS2 were note related. It follows therefrom that URS1 and URS2 merely inhibit activity of the UAS-related factors and are not involved in the promoter transcription regulation by carbon source.

The mutant AOX2 promoter of the present invention has a markedly enforced promoter activity as compared with wild-type AOX2 promoters. Accordingly, the promoter of the present invention is highly utilizable as a promoter for a vector capable of expressing a heterologous protein. The vector of the present invention can efficiently express and produce various useful heterologous proteins in hosts.

What is claimed is:

1. A mutant AOX2 promoter wherein 1 to 3 copies of the oligonucleotide GATAGGCTATTTTTGTCGCATAAAT (SEQ ID NO: 2) is (are) added in the forward orientation, the reverse orientation or in both the forward and reverse orientations at the 5' end of a partial DNA fragment of a wild-type AOX2 promoter of *Pichia pastoris*.

2. The mutant AOX2 promoter of claim 1, wherein the partial DNA fragment comprises at least nucleotides 1325–1528 of SEQ ID NO: 1.

3. The mutant AOX2 promoter of claim 2, further comprising nucleotides 1–1324 of SEQ ID NO:1, wherein at least one base of nucleotides 1–1324 is substituted or deleted, or at least one base is added to nucleotides 1–1324.

4. The mutant AOX2 promoter of claim 1, wherein the partial DNA fragment comprises at least nucleotides 1274–1528 of SEQ ID NO: 1.

5. The mutant AOX2 promoter of claim 4, further comprising nucleotides 1–1273 of SEQ ID NO:1, wherein at least one base of nucleotides 1–1324 is substituted or deleted, or at least one base is added to nucleotides 1–1324.

6. The mutant AOX2 promoter of claim 1, wherein the partial DNA fragment comprises at least nucleotides 1192–1528 of SEQ ID NO: 1.

7. The mutant AOX2 promoter of claim 6, further comprising nucleotides 1–1191 of SEQ ID NO:1, wherein at least one base of nucleotides 1–1324 is substituted or deleted, or at least one base is added to nucleotides 1–1324.

8. The mutant AOX2 promoter of claim 1, wherein the partial DNA fragment comprises at least nucleotides 845–1528 of SEQ ID NO: 1.

9. The mutant AOX2 promoter of claim 8, further comprising nucleotides 1–844 of SEQ ID NO:1, wherein at least one base of nucleotides 1–1324 is substituted or deleted, or at least one base is added to nucleotides 1–1324.

10. The mutant AOX2 promoter of any one of claims 1, 4, 6, 8 or 3, wherein at least one base of nucleotides 1274–1314 is substituted or deleted, or at least one base is added to nucleotides 1274–1314.

11. The mutant AOX2 promoter of any one of claims 1, 6, 8, 3 or 5, wherein at least one base of nucleotides 1192–1216 is substituted or deleted, or at least one base is added to nucleotides 1192–1216.

12. The mutant AOX2 promoter of any one of claims 1, 2, 4, 6, 3 or 5 comprising:

a) substitution of the 1274th thymine with cytosine, b) addition of nucleotides 1296–1314 between the 1314th nucleotide and 1315th nucleotide, c) substitution of the 1209th guanine with thymine, d) substitution of the 1212th thymine with guanine, e) substitution of the 1193rd adenine with guanine or f) substitution of the 1195th adenine with guanine.

13. A vector carrying the mutant AOX2 promoter of claim 1.

14. The vector of claim 13, comprising a structural gene of a heterologous protein under the transcription regulation of the mutant AOX2 promoter.

15. The vector of claim 14, wherein the structural gene is selected from the group consisting of human serum albumin, prourokinase, tissue plasminogen activator and interferon.

16. A transformant transformed with the vector of any one of claims 13 to 15.

17. The transformant of claim 16, wherein the transformant is *Pichia pastoris*.

18. A method for producing a heterologous protein, comprising culturing the transformant of claim 17 and collecting a heterologous protein from the culture thereof.

\* \* \* \* \*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
    ( A ) LENGTH: 1528 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc = "Plasmid DNA"

( x i ) SEQUENCE DESCRIPTION: SEQ ID NO:1:

```
AATTCTTTTT TTCAGACCAT ATGACCGGTC CATCTTCTAC GGGGGGATTA TCTATGCTTT      60
GACCTCTATC TTGATTCTTT TATGATTCAA ATCACTTTTA CGTTATTTAT TACTTACTGG    120
TTATTTACTT AGCGCCTTTT CTGAAAAACA TTTACTAAAA ATCATACATC GGCACTCTCA    180
AACACGACAG ATTGTGATCA AGAAGCAGAG ACAATCACCA CTAAGGTTGC ACATTTGAGC    240
CAGTAGGCTC CTAATAGAGG TTCGATACTT ATTTGATAA TACGACATAT TGTCTTACCT     300
CTGAATGTGT CAATACTCTC TCGTTCTTCG TCTCGTCAGC TAAAAATATA ACACTTCGAG    360
TAAGATACGC CCAATTGAAG GCTACGAGAT ACCAGACTAT CACTAGTAGA ACTTTGACAT    420
CTGCTAAAGC AGATCAAATA TCCATTTATC CAGAATCAAT TACCTTCCTT TAGCTTGTCG    480
AAGGCATGAA AAAGCTACAT GAAAATCCCC ATCCTTGAAG TTTTGTCAGC TTAAAGGACT    540
CCATTTCCTA AAATTTCAAG CAGTCCTCTC AACTAAATTT TTTTCCATTC CTCTGCACCC    600
AGCCCTCTTC ATCAACCGTC CAGCCTTCTC AAAAGTCCAA TGTAAGTAGC CTGCAAATTC    660
AGGTTACAAC CCCTCAATTT TCCATCCAAG GGCGATCCTT ACAAAGTTAA TATCGAACAG    720
CAGAGACTAA GCGAGTCATC ATCACCACCC AACGATGGTG AAAAACTTTA AGCATAGATT    780
GATGGAGGGT GTATGGCACT TGGCGGCTGC ATTAGAGTTT GAAACTATGG GGTAATACAT    840
CACATCCGGA ACTGATCCCA CTCCGAGATC ATATGCAAAG CACGTGATGT ACCCCGTAAA    900
CTGCTCGGAT TATCGTTGCA ATTCATCGTC TTAAACAGTA CAAGAAACTT TATTCATGGG    960
TCATTGGACT CTGATGAGGG GCACATTTCC CCAATGATTT TTTGGGAAAG AAAGCCGTAA   1020
GAGGACAGTT AAGCGAAAGA GACAAGACAA CGAACAGCAA AAGTGACAGC TGTCAGCTAC   1080
CTAGTGGACA GTTGGGAGTT TCCAATTGGT TGGTTTTGAA TTTTACCCA TGTTGAGTTG    1140
TCCTTGCTTC TCCTTGCAAA CAATGCAAGT TGATAAGACA TCACCTTCCA AGATAGGCTA   1200
TTTTTGTCGC ATAAATTTTT GTCTCGGAGT GAAAACCCCT TTTATGTGAA CAGATTACAG   1260
AAGCGTCCTA CCCTTCACCG GTTGAGATGG GGAGAAAATT AAGCGATGAG GAGACGATTA   1320
TTGGTATAAA AGAAGCAACC AAAATCCCTT ATTGTCCTTT TCTGATCAGC ATCAAAGAAT   1380
ATTGTCTTAA AACGGGCTTT TAACTACATT GTTCTTACAC ATTGCAAACC TCTTCCTTCT   1440
ATTTCGGATC AACTGTATTG ACTACATTGA TCTTTTTTAA CGAAGTTTAC GACTTACTAA   1500
```

ATCCCCACAA ACAAATCAAC TGAGAAAA  1528

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Plasmid DNA"

(xi) SEQUENCE DESCRIPTION: SEQ ID NO:2:

GATAGGCTAT TTTTGTCGCA TAAAT  25

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Plasmid DNA"

(xi) SEQUENCE DESCRIPTION: SEQ ID NO:3:

AAATTAAGCG ATGAGGAGA  19

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:4:

GAATTCACTA AGCGAGTCAT CATC  24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:5:

GAATTCCAGC TGTCAGCTAC CTAG  24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:6:

GAATTCCCAA GTAGGCTATT TTTG                24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:7:

GAATTCTACA GAAGCGTCCT ACCC                24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:8:

GAATTCCGAT TATTGGTATA AAAG                24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:9:

TTCGAAGTTT TTCTCAGTTG ATTT                24

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:10:

CCGGATCCAC TAAGCGAGTC ATCATC                26

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:11:

```
CCGAATTCGA CAATATTCTT TGATGC                                                    26
```

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:12:

```
GAATTCCCAA GATAGGCTAT TTTTG                                                     25
```

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:13:

```
TTCGAAGTTT TTCTCAGTTG ATTTGTTTGT GGGGAT                                         36
```

( 2 ) INFORMATION FOR SEQ ID NO:14:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:14:

```
AATTCGATAG GCTATTTTG TCGCATAAAT G                                               31
```

( 2 ) INFORMATION FOR SEQ ID NO:15:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:15:

```
AATTCATTTA TGCGACAAAA ATAGCCTATC G                                              31
```

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:16:

CACCTTCCAA GGTGGGCTAT TTTTG  25

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:17:

CTATTTTTGT CTCAGAAATT TT  22

(2) INFORMATION FOR SEQ ID NO:18:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:18:

TTGATAAGAC ATCACCTTCC AAGGTGGGCT ATTTTGTCG CATAAATTTT  50

(2) INFORMATION FOR SEQ ID NO:19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:19:

TTGATAAGAC ATCACCTTCC AAGATAGGCT ATTTTGTCT CAGAAATTTT  50

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:20:

GAATTCCCAA GATAGGCTAT TTTTG  25

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:21:

```
TTCGAAGTTT TTCTCAGTTG ATTTGTTTGT GGGGAT                                                    36
```

( 2 ) INFORMATION FOR SEQ ID NO:22:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:22:

```
TGCTGATAGC CTAACGTTCA TGATCAAAA                                                            29
```

( 2 ) INFORMATION FOR SEQ ID NO:23:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:23:

```
AAGCGATAGA GAGACTGCGC TAAGCATTAA TG                                                        32
```